(12) United States Patent
Spartz et al.

(10) Patent No.: US 9,606,088 B2
(45) Date of Patent: Mar. 28, 2017

(54) PROCESS AND SYSTEM FOR RAPID SAMPLE ANALYSIS

(71) Applicant: Prism Analytical Technologies, Inc., Mt. Pleasant, MI (US)

(72) Inventors: Martin L. Spartz, Ellington, CT (US); Anthony S. Bonanno, Ellington, CT (US); Peter P. Behnke, Ellington, CT (US)

(73) Assignee: Prism Analytical Technologies, Inc., Mt. Pleasant, MI (US)

( * ) Notice: Subject to any disclaimer, the term of this patent is extended or adjusted under 35 U.S.C. 154(b) by 1 day.

(21) Appl. No.: 14/660,574

(22) Filed: Mar. 17, 2015

(65) Prior Publication Data
US 2015/0260695 A1    Sep. 17, 2015

Related U.S. Application Data

(60) Provisional application No. 61/954,054, filed on Mar. 17, 2014.

(51) Int. Cl.
G01N 21/31    (2006.01)
G01N 21/35    (2014.01)
(Continued)

(52) U.S. Cl.
CPC .......... G01N 30/74 (2013.01); G01J 3/42 (2013.01); G01N 21/3504 (2013.01); G01N 30/8606 (2013.01); G01N 30/8641 (2013.01); G01N 21/031 (2013.01); G01N 21/33 (2013.01); G01N 21/359 (2013.01); G01N 21/3581 (2013.01);
(Continued)

(58) Field of Classification Search
CPC .............. G01J 3/42; G01N 2021/3595; G01N 2030/008; G01N 2030/025; G01N 2030/743; G01N 21/031; G01N 21/33; G01N 21/3504; G01N 21/3581; G01N 21/359;
(Continued)

(56) References Cited

U.S. PATENT DOCUMENTS 3,735,565 A    5/1973   Gilby et al.
5,039,614 A    8/1991   Dekmezian et al.
(Continued)

FOREIGN PATENT DOCUMENTS

EP    0 187 306 A2    7/1986
WO    93/03493 A1     2/1993

OTHER PUBLICATIONS

"TDT Air Scan: The determination of over 400 Volatile Organic Compounds (VOCs) using a single, simple-to-use air test." Bulletin 908-0611, Prism Analytical Technologies, 2011. 2 pages.
(Continued)

Primary Examiner — Mark R Gaworecki
(74) Attorney, Agent, or Firm — HoustonHogle LLP

(57) ABSTRACT

Components resolved in time by a separator accumulate in a sample cell and are analyzed by electromagnetic radiation-based spectroscopic techniques. The sample cell can be configured for multiple path absorption and can be heated. The separator can be a gas chromatograph or another suitable device, for example a distillation-based separator. The method and system described herein can include other mechanical elements, controls, procedures for handling background and sample data, protocols for species identification and/or quantification, automation, computer interfaces, algorithms, software or other features.

14 Claims, 16 Drawing Sheets

(51) Int. Cl.
    *G01J 3/42*     (2006.01)
    *G01N 30/74*     (2006.01)
    *G01N 30/86*     (2006.01)
    *G01N 21/3504*     (2014.01)
    *G01N 21/03*     (2006.01)
    *G01N 30/00*     (2006.01)
    *G01N 30/02*     (2006.01)
    *G01N 21/33*     (2006.01)
    *G01N 21/3581*     (2014.01)
    *G01N 21/359*     (2014.01)
    *G01N 21/64*     (2006.01)
    *G01N 21/65*     (2006.01)

(52) U.S. Cl.
    CPC .............. *G01N 21/64* (2013.01); *G01N 21/65* (2013.01); *G01N 2021/3595* (2013.01); *G01N 2030/008* (2013.01); *G01N 2030/025* (2013.01); *G01N 2030/743* (2013.01)

(58) Field of Classification Search
    CPC ........ G01N 21/64; G01N 21/65; G01N 30/74; G01N 30/8606; G01N 30/8641
    See application file for complete search history.

(56) References Cited

U.S. PATENT DOCUMENTS 8,180,203 B2     5/2012     Kurano
2007/0273882 A1     11/2007     Smith
2011/0054804 A1     3/2011     Pfaff

OTHER PUBLICATIONS

Doussin, Jean-Francois, et al. "Multiple-pass cell for very-long-path infrared spectrometry." Applied Optics, vol. 38, No. 19 (Jul. 1, 1999). pp. 4145-4150.

Liu, Michael X., et al. "Quantitative Analysis of Copolymers by GPC/FT-IR." Applied Spectroscopy, vol. 50, No. 3 (1996). pp. 349-356.

International Search Report and Written Opinion of the International Searching Authority, mailed on Jun. 24, 2015, from counterpart International Application No. PCT/US2015/021046, filed on Mar. 17, 2015.

International Preliminary Report on Patentability, mailed on Sep. 29, 2016, from International Application No. PCT/US2015/021046, filed on Mar. 17, 2015. Twelve pages.

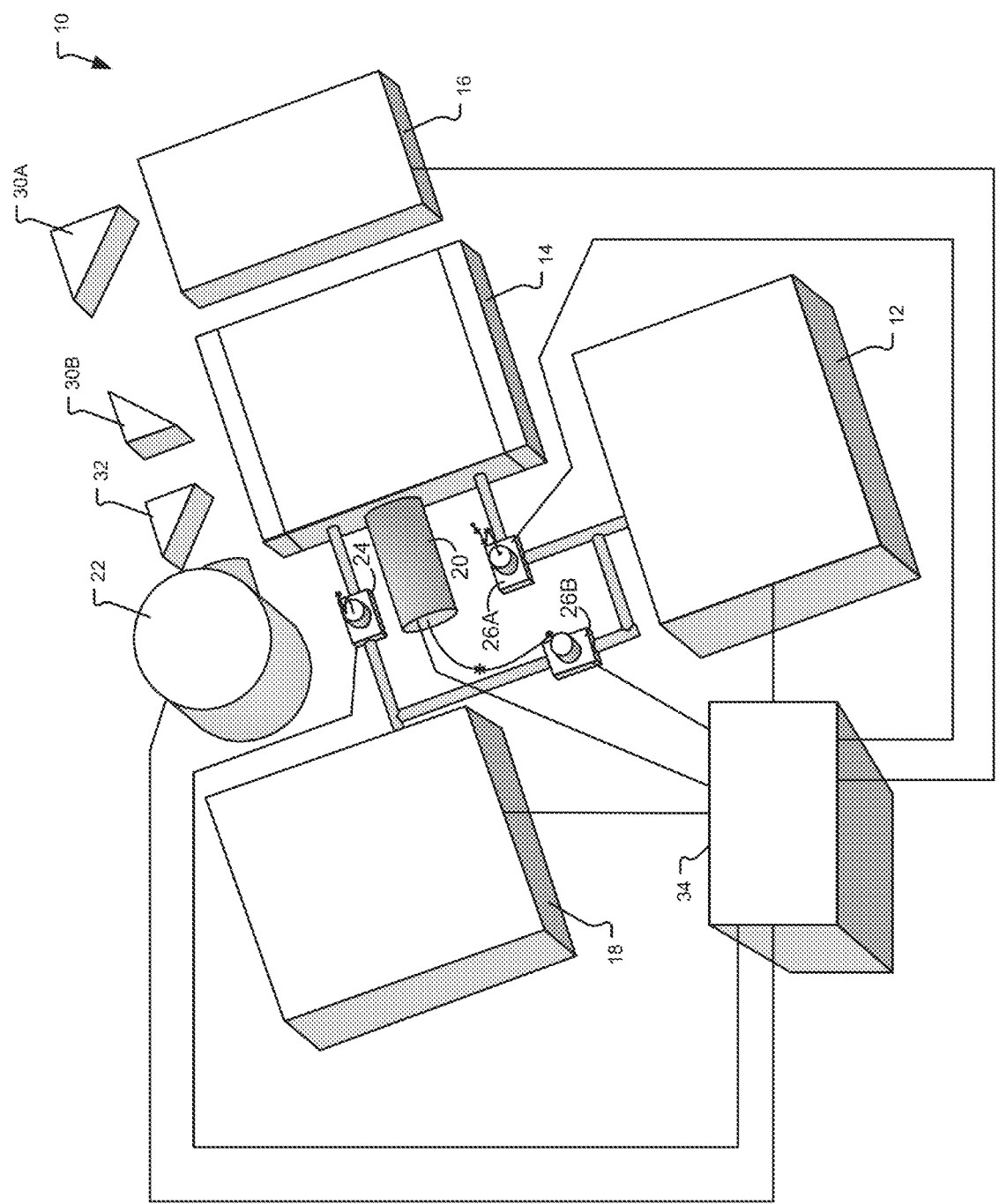

PROCESS AND SYSTEM FOR RAPID SAMPLE ANALYSIS

RELATED APPLICATIONS

This application claims the benefit under 35 USC 119(e) of U.S. Provisional Application No. 61/954,054, filed on Mar. 17, 2014, which is incorporated herein by reference in its entirety.

BACKGROUND OF THE INVENTION

Gas Chromatography (GC) is used to resolve a mixture into its various components according to retention profiles of the different molecules passing through the GC column. While the technique can separate mixtures containing hundreds of substances, identifying the molecules that elute from the column is more problematic. To address the need for rapid and sensitive identification of the molecular species present, GC has been integrated with techniques such as mass spectrometry (MS) or Fourier transform infrared (FTIR) spectrometry.

Gas chromatography-mass spectrometry (GC-MS) is probably the most widespread tandem technique in the analytical instrumentation industry today. GC-MS systems are versatile and are employed across many different industries, particularly for environmental, chemical, petroleum, pharmaceutical, and toxicological applications. While GC-MS is a fast, sensitive technique suitable for multiple component detection and spectral identification, capable of measuring atomic species and supported by large available spectral libraries, it suffers from many disadvantages. These include compound separation to prevent MS interferences, non-linear calibrations, poor precision and accuracy (requiring constant calibration) and limited dynamic range. Problems also are encountered when high concentrations are present that can allow for chemical ionization to occur, generating questionable data.

To prevent MS spectral overlaps and interferences, the technique typically requires fully or nearly fully resolved GC peaks, with limited to no co-elution. Also GC-MS cannot differentiate between structural isomers that have identical electron impact and chemical ionization mass spectra. Moreover, most GC-MS systems require user selection of a list of compounds prior to analysis (e.g., approximately 60) and then only report those. Although the MS software can then do a global search and try to identify other peaks, it can seldom perform a quantitative analysis. This may be due, at least in part, to the fact that, although extensive (10,000s), MS libraries are only qualitative and can differ from one MS manufacturer to another. Thus unless the MS is calibrated for a compound, a semi-quantitative analysis remains the best outcome for a detected peak.

GC-MS systems are also somewhat temperamental. For analysis, GC-MS normally requires helium or hydrogen gases, which raise cost and/or safety considerations. Equipment problems can arise with atmospheric leaks due to low operating pressures and, in general, GC-MS systems tend to require frequent maintenance, leading to extensive downtime. Then, bringing the systems back on-line can be time consuming and labor intensive.

While GC-MS is the more commonly deployed solution, Gas Chromatography-Fourier Transform Infrared Spectrometry (GC-FTIR) provides a powerful analytical tool that is particularly useful to distinguish among structural isomers that have identical electron impact and chemical ionization mass spectra.

SUMMARY OF THE INVENTION

Nevertheless, the designs of existing GC-FTIR systems are also plagued with their own limitations. For example, many GC-FTIR couplings utilize a "light pipe" (typically a cell or cuvette used for passing both gas eluted from the GC column, and light from the FTIR interferometer). The light pipe is made relatively short to prevent peak dilution through the IR cell and its eventual IR detection or secondary detection. Since IR absorption is proportional to cell path length, this short path length limits the sensitivity (minimum detection limit (MDL)) of the technique. Problems also arise in cases in which GC peaks come off very quickly. Since the light pipe has a relatively large volume when compared to the flow rates of the GC, the gas can become diluted, making measurements more difficult.

A need exists, therefore, for techniques and equipment that address problems presented by conventional GC-MS or GC-FTIR techniques and systems. For example, there is a need for coupling existing or newly developed systems that discriminate or resolve species in time, such as GCs, and/or optical spectroscopy systems, such as FTIRs, in ways that reduce or minimize the deficiencies encountered with conventional light pipe arrangements. A need exists as well for simple units and procedures that can integrate GCs with other spectroscopic methods suitable for identifying component species. Also desirable is the integration of separation techniques other than GC with FTIR or other spectroscopic analytical tools.

Generally the invention relates to a system and method that couple a time-resolved separator, in many cases a gas chromatograph (GC), to an analyzer that relies on optical spectroscopic technology such as FTIR or other spectroscopy technology.

In many of its embodiments the coupling between separator and optical spectroscopic analyzer is based on a sample cell having particular features. The electromagnetic-based radiation spectroscopic device can be used to identify and, in many cases, quantify the species present in the components (peaks) resolved by the separator. Controls, automation instrumentation, computer interfaces, algorithms and/or software-related features also can be provided.

In one aspect, a method for analyzing a sample comprises directing output from a temporally-resolved separator to a sample cell, e.g., a gas cell that integrates the components provided by the separator. Typically, the sample cell has been partially or fully evacuated. Fluids, e.g., gas(es) are allowed to accumulate in the sample cell, effectively integrating their spectral signatures. Multiple spectra obtained over a time interval can then be averaged to best measure the integrated concentration in the sample cell. Obtaining a moving background that includes spectra from a previously eluted sample component, e.g., previously eluted chemical species, allows for the analysis of the current eluting components without interference from previously eluted components. The integrated and averaged multiple spectra can be corrected by using a similarly collected moving background and the corrected data are compared to known spectra to identify one or more components, e.g., chemical species such as atoms, molecules, molecular fragments, ions, present in the current sample component.

In another aspect, a system for analyzing a sample includes a sample cell coupling a separator that resolves sample components in time and a spectroscopic analyzer, wherein the sample cell is configured for integrating a sample component generated by the separator and may average the collected spectra during or after each integration is complete. In some embodiments, resultant sample data, corrected using a background that can be a described time before the elution time, are analyzed for certain compounds expected to elute at that time.

In specific implementations the sample cell is heated. In others it is also configured for multiple path absorption.

The separator can be a gas chromatograph, a distillation-based separator or another suitable unit that can temporally resolve or separate components, such as chemical species, present in a sample. While in the current embodiment the separator is a gas chromatography system, in other embodiments separators such as liquid chromatography systems, affinity chromatography systems, supercritical fluid chromatography systems, ion exchange chromatography systems, distillation systems, fractional distillation systems, thermal desorption systems, pseudo distillation apparatuses, thermogravimetric analysis (TGA) instruments or pyrolysis instruments are employed.

In general, according to one aspect, the invention features a sample analysis system. This system comprises a separator that provides components of a sample over time, a sample cell in which the components are integrated, e.g., collected and accumulated, and a spectroscopy system for obtaining a spectral response of the components in the sample cell.

In different implementations, the spectroscopy system determines the spectral response of the components in the sample cell in one or more of the following spectral regions millimeter, microwave, terahertz, infrared (including near-, mid- and/or far-infrared), visible, ultraviolet (UV) (including vacuum ultraviolet (VUV)), x-rays and/or gamma. Further, the spectroscopy system can measure different characteristics, such as absorption spectra, emission (including blackbody or fluorescence) spectra, elastic scattering and reflection spectra, impedance (e.g., index of refraction) spectra, and/or inelastic scattering (e.g., Raman and Compton scattering) spectra of the components in the sample cell.

When the separator is a gas chromatography system, it may not require a separate detection system.

In one embodiment, the spectroscopy system is a Fourier transform infrared spectrometer.

Preferably, a path length in the sample cell is increased by a multiple path optical arrangement. A White cell or modified White cell type optical arrangement can be used.

Embodiments can include a vacuum pumping device for evacuating or partially evacuating the sample cell. Further, a valve for isolating the sample cell from a pumping device, a valve for diverting output from the separator away from the sample cell, a sample cell pressure control, or any combination thereof can be used.

A sample concentrating device, such as a TDT, purge and trap or a solvent concentrating device, can be used for collecting the sample.

In general according to another aspect, the invention features a sample analysis method, which comprises providing components of a sample over time, collecting the components in a sample cell, and obtaining a spectral response of the components in the sample cell.

In general according to another aspect, the invention features a sample cell system. This system comprises a sample cell for integrating components, an input port for receiving components from a separator into the sample cell, and a spectral analysis path for transporting energy though the sample cell to enable the determination of a spectral response of the components in the cell.

Usually, the sample cell is at least partially evacuated.

In general according to another aspect, the invention features a method for using a sample cell. This method comprises integrating components in the sample cell, periodically determining spectral responses of the components in the cell, and using some of the spectral responses as backgrounds to analyze more recent spectral responses to identify the components.

In general according to another aspect, the invention features a system for analyzing a sample. This system comprises a sample cell for integrating components and analyzing samples, a spectroscopy system determining spectral responses of the components in the sample cell over time, and a computer system comparing the spectral responses to identify and/or quantify the components in the sample cell.

In general according to another aspect, the invention features a method for analyzing a sample. This method comprises integrating eluted components from the sample in a sample cell, determining spectral responses of the components in the sample cell over time, and comparing the spectral responses to identify and/or quantify the components in the sample cell.

In general according to another aspect, the invention features a system for analyzing a sample. This system comprises a gas chromatography system for eluting components of a sample, a sample cell for collecting and integrating the components, a valve device between the gas chromatography system and the sample cell that is opened for periods to release slugs of effluent into the sample cell, and a spectroscopy system determining spectral responses of the components in the sample cell.

Here, the valve device can be a standard valve or a mass flow controller, for example.

In general according to another aspect, the invention features a method for analyzing a sample. This method comprises eluting components of a sample from a separator, collecting and integrating the components in a sample cell, periodically releasing effluent from the separator into the sample cell, and determining spectral responses of the components in the sample cell.

In general according to another aspect, the invention features a computer system for analyzing a sample. This computer system controls the generation of components from a sample and their accumulation in a sample cell. The computer receives spectral responses of the components from a spectroscopy system and compares those spectral responses to previously generated spectral responses to identify and/or quantify the components in the sample cell.

In general according to still another aspect, the invention features a method for analyzing a sample. This method comprises generating components from a sample and acquiring spectral responses of the components over time and comparing the spectral responses to previously generated spectral responses to identify and/or quantify newly generated components.

Practicing the invention can have many advantages. In some of its aspects, the system and method described herein can be used to detect any optically, such as IR, active vapor or gas. Many spectral resolutions are available depending on the specific application, and the technique can measure organics, inorganics, polars, non-polars, acids and bases on the same system. Low molecular to very high molecular weight compounds can be detected. In comparison to GC-MS, full spectral identification and quantification are possible, including the capability of measuring isotopes or structural isomers. Information about chemical functionalities (e.g., alcohol, ester, ether, ketone, acid, amine, halogen presence, and so forth) present also can be obtained. Typically, the spectra generated are constant, with no cross interaction between species. Moreover, advantages are realized since a technique such as GC-FTIR can measure or deconvolve many compounds that co-elute. 20+ compounds have been demonstrated but more are certainly possible with advanced analysis algorithms. Significantly, inorganic gases that are not retained by the GC column can be measured simultaneously and without interference. Overlapping compounds also can be measured because interferences can be removed (blended into the background spectrum) as a run progresses.

Furthermore, low level compounds can be measured in the presence of high concentration compounds, up to 9 orders of magnitude or even higher. The technique can handle very heavily concentrated samples from direct injection, purge and trap or thermal desorption tubes. In fact, it appears that the system designed herein cannot be saturated with too much sample.

Conventionally, high volume injection ports are used with detectors capable of handling larger sample sizes such as flame ionization detector (FID), thermal conductivity detector (TCD), electron capture detector (ECD), electrolytic conductivity detector (ELCD) or nitrogen-phosphorus detector (NPD). These, however, cannot provide qualitative spectra. On the other hand, MS detection is not typically used in conjunction with high volume injections arrangements, since it requires splitting the sample to reduce loading. In contrast, large solvent peaks will not necessarily damage the system described herein, since there is no filament or detector in contact with the gases to damage or potentially burn out. As a result, there is no need to split the sample injected into a GC separator and relatively large injection volumes are possible. Loss of peak resolution due to larger samples is also a non-factor since each peak will be integrated over time. Problems associated with chemical ionization and other ion interactions at higher concentrations are also eliminated.

Whereas existing approaches measure peak signal, embodiments of the system and method described herein provide an integration of the peak signal, enhancing signal-to-noise ratios (SNR) over existing technology. As further described below, some spectra can be chosen for background and others for compound measurements as a gas enters and fills a sample cell, resulting in integral effects compared to conventional approaches. Significant SNR advantages also are realized when all of a component gas is monitored at the end of its elution peak.

Since the sample is integrated, the chromatography does not present as important an issue and approaches disclosed herein can allow for broader GC peaks without loss in detection limit, yielding the same results regardless of the chromatography. Comparing the same sample separated in a short column with one separated in a long column yielded basically the same results. Thus the integrating nature of the present techniques and system allows having one calibration that could be used on any separation device.

In many cases, full resolution of peaks generated by the separator is not required. Moreover, this makes possible utilizing separators that resolve mixture components to a lesser extent than is more characteristic of most GC-MS systems (e.g., shorter columns, larger diameter columns, packed columns and so forth could be incorporated). One implementation described herein includes a "pseudo distillation" separator capable of working with very large samples. In turn, this can result in very low MDLs (e.g., <1 µg/µl in the original sample).

Systems and techniques described herein can reach MDLs that are at, near, or below corresponding GC-MS systems without the MS detector drawbacks. For instance, low MDLs are expected with samples collected on Thermal Desorption Tubes (TDT), solvent concentrates, or purge and trap systems. MDLs can be automatically determined for each compound in a library during each sample analysis. For instance, air samples can be collected onto a TDT, e.g., at a flow rate of 100 mL/minute, for long periods of times, e.g., hours, or even days depending on the material being trapped, allowing for % to ppt (parts per trillion) or lower detection limits for compounds found in the ambient air. Sample collection is easy, inexpensive and contains no complicated mechanical parts for opening or closing the tube. In many aspects, flows can be set, preset and/or, maintained at a constant rate and samples can be collected without operator oversight over a predefined time frame.

The GC-FTIR technique and system disclosed herein can, in many cases, outperform GC-MS, if such performance is required. Unlike in MS-based approaches, optical or IR spectral calibrations can be constant for the life of the instrument or type of spectrometer. Once established, e.g., by operator or instrument supplier, the need for recalibration is expected to be low or non-existent. Due to the IR absorption spectrum for each component remaining constant or near constant for most compounds at a constant temperature. A change in pressure can affect some very light molecules absorption profile but additional data could be added to the library to make corrections for any pressure change. Component integration in the gas cell further reduces any calibration variability from changes in the chromatography or separation. Thus a spectral library can be constructed that is constant in qualitative and quantitative nature and can be transferred between like instruments with widely ranging separation systems.

Whereas MS libraries are primarily qualitative, spectral libraries used, e.g., in FTIR analysis if collected correctly, are fully quantitative. Unlike GC-MS, the approach described herein also allows monitoring for every compound in a library as the chromatography, separation or distillation progresses.

Many spectral calibrations can be very linear throughout entire analysis ranges and no further calibration may be required after initial the calibration by manufacturer or customer. Percent to parts per trillion or less measurements can be obtained with the same configuration with no modifications.

Generally, the system described herein is rugged, requires limited service, with quick starts and restarts. It can be used in the field without concerns regarding instrument damage or long warm-up periods. Advantageously, the chromatography can run on $N_2$. Pressures can be from near zero up to and potentially exceeding atmospheric. Some embodiments disclosed herein do not require helium, hydrogen, turbo pumps, electron ionization (EI) sources, or secondary GC detection devices, simplifying instrument operation and maintenance requirements. In many of its implementations, the invention allows any GC supplier or user to couple an existing GC to any commercial FTIR or other spectroscopic instrument.

Other advantages relate to the moving background described herein, since any change in the spectrometer response, possible especially during a long run, is removed. Without this feature, a baseline change that is in any way not a linear change affects the detection of low level compounds since the peak would be less than the compound peak size. Thus late eluters would be compared to a background that is moving around and changing and since late eluters are diffusing in the sample (gas) cell, the peak will be drawn out, giving the appearance of a baseline shift at long times. These two issues are addressed by the integration and background shifting disclosed herein.

The above and other features of the invention including various details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIGS. 2A and 2B are schematic diagrams of a sample analysis system (e.g., GC-FTIR) system according to embodiments of the invention.

FIG. 12B shows a reporting method having mass (ng) or concentration on the y-axis and compounds shown as a single line (bar graph) at their respective R.I. (Retention Index).

DETAILED DESCRIPTION OF THE PREFERRED EMBODIMENTS

Figure 1:
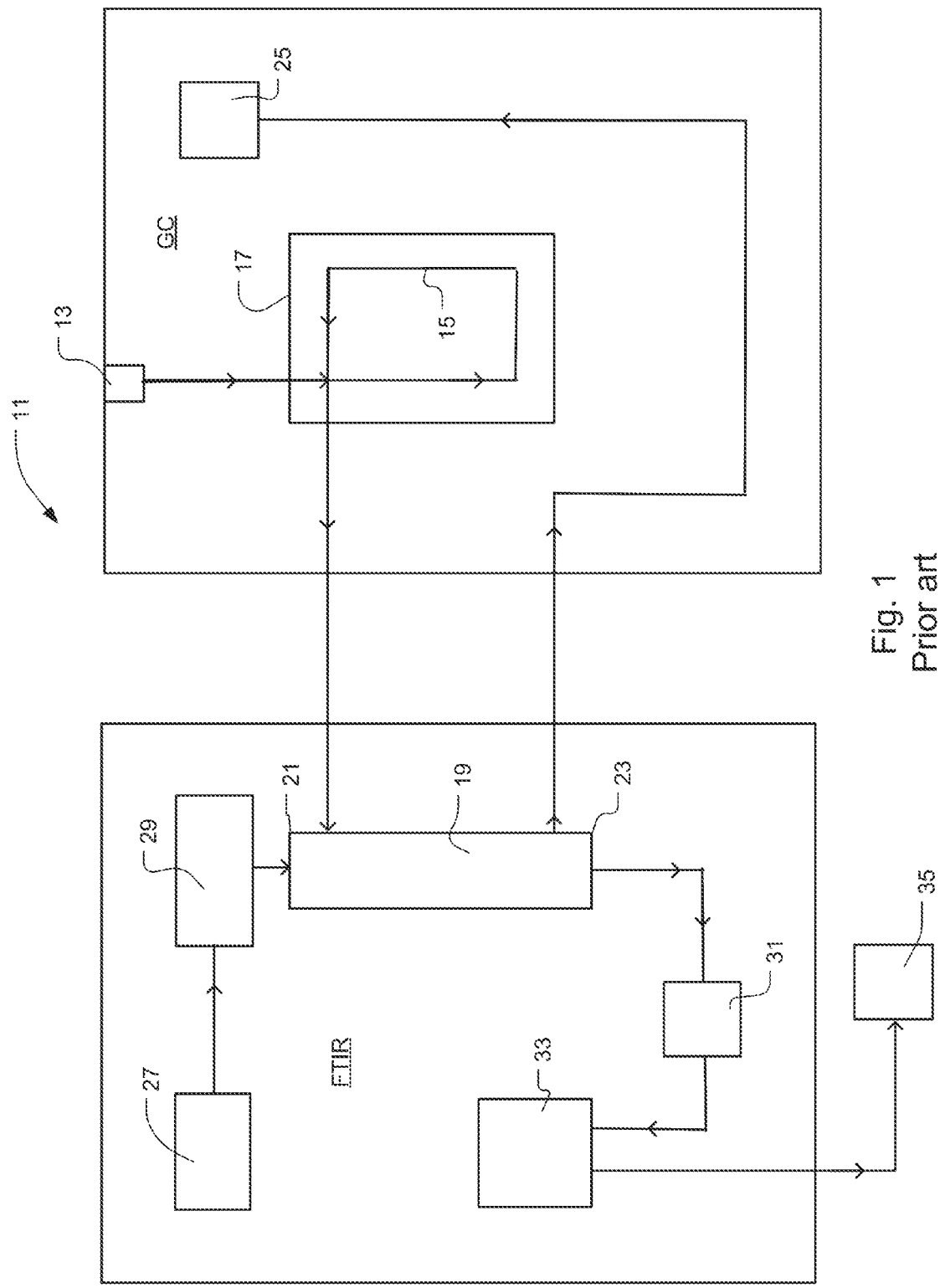
FIG. 1 is a schematic diagram of a conventional GC-FTIR system that uses a "light pipe" optical gas cell.

Many existing arrangements that involve a GC and FTIR analyzer couple the two via a light pipe optical gas cell. Shown in FIG. 1, for example, is system 11 including GC and FTIR sections.

During operation, a sample is injected at injection port 13 of the GC section, and directed through GC column 15, typically heated by oven 17. Output from the column enters light pipe 19 (often heated by an oven, not shown in FIG. 1 near end 21), exits the light pipe near end 23 and is sometimes directed to a secondary GC detector 25, usually a flame ionization detector (GC-FID) or thermal conductivity detector (TCD). A FID detector relies on a hydrogen/air flame to oxidize organic molecules and produce electrically charged particles (or ions). A TCD relies on the difference of thermal conductivity between the carrier and sample analyte gas to sense eluting components.

In the FTIR section of arrangement 11, IR generated by source 27 and modified according to the principles of Fourier transform spectrometry, using device 29, typically a Michelson interferometer, is directed to end 21 of light pipe 19 and exits the light pipe at end 23, both ends being provided with IR transparent windows.

From the light pipe, output radiation is directed to IR detector 31, usually a mercury cadmium telluride (MCT) detector. Signals generated and data are typically handled by electronics 33 and processing equipment 35.

The present invention generally relates to techniques and equipment for analyzing a sample, typically a mixture containing more than one distinct chemical species. Components in the sample can be separated through techniques such as gas chromatography or another suitable separation method, for example a distillation or distillation-like process or other process that resolves the different chemical species in time. Chemical identification of the species present in the sample is carried out by optical spectroscopy, such as, for instance, FTIR. Coupling between separator and analyzer is through a sample cell having one or more features further described below.

Shown in FIGS. 2A and 2B, for example, is system 10, including a separator such as gas chromatograph (GC) 12, sample cell 14, for instance a multiple pass cell such as a White cell or modified White cell with aspherical optics, further described below, and a spectrometer, e.g., FTIR spectrometer 16, which includes a light, more generally EM radiation, source. In specific implementations, GC 12 and/or FTIR spectrometer 16 are commercially available instruments, with exhaust from the GC being often directly coupled to the FTIR sample cell.

In general, the GC uses a stationary phase, which is typically a microscopic layer of liquid or polymer on an inert solid glass or metal tube, i.e., a column. The mobile phase is a carrier gas, usually an inert gas such as helium or an unreactive gas such as nitrogen. The carrier gas flow is controlled by flow controllers and/or a series of valves to maintain or vary the flow rate during the separation. The flow controllers and valves can also be utilized to allow the entire sample or a fraction of the sample to enter the column. The column is located in an oven where the temperature of the gas passing through the column can be controlled. The gaseous compounds interact with the walls of the column or stationary phase, causing each compound to elute at a different time, known as the retention time of the compound.

In other embodiments, instead of a GC separator, another type of separator is used such as a liquid chromatography system, affinity chromatography system, supercritical fluid chromatography system, ion exchange chromatography system, distillation system, fractional distillation system, thermal desorption system, thermogravimetric analyzer, pyrolysis instrument, or pseudo distillation apparatus.

In the example of a GC separator 12, it can be operated with or without typical GC detection, e.g., with or without the FID/TCD/MSD (mass spectrometer detector) arrangement mentioned above. Examples of GC columns that can be used include but are not limited to current small bore (e.g. 0.20-0.75 mm outer diameter (OD)) capillary columns, traditional packed columns (⅛ inch; ¼ inch OD), short packed ¼ inch OD glass or stainless steel (SS) columns, wide or mega-bore (mm OD) columns, packed or mega-bore (mm OD) coated columns and so forth.

The sample can be introduced to GC 12 via an injection arrangement such as a direct injection port, or static or flow-through sample loops. In many cases the subsequent sample injection requires no sample split and can be, for example, on column or split-less. In some embodiments, the injection arrangement incorporates elements suitable for concentrating the sample. Examples include but are not limited to thermal desorption tubes (TDTs), purge and trap systems (using cold or cryo traps), solvent concentration arrangements and so forth. Sample volumes can be the standard direct injection volumes of about 1 microliter (μL) used in conventional GC-MS equipment or significantly larger injection volumes (eg. 100+ μL). In many embodiments, and in particular in conjunction with larger GC columns or a separator such as the pseudo distillation separator further described below, system 10 can handle considerably larger direct injection samples, e.g., from about 100 μL to about 1 mL.

Some approaches can utilize Programmed Temperature Vaporizing (PTV or PVT), a widely used technique to slowly vaporize large samples so that the solvent is boiled off and typically diverted from the GC column, leaving the higher boiling material to condense near or at the beginning of the column. In one example the injection system is a MultiMode Inlet system produced by OPTIC. The current version (OPTIC-4), for instance can be used for hot injections, cold injections, large volume, on-column injections, in liner derivatisation, thermal desorption, pyrolysis and so forth. The design of the injector body of this type of injection system is described, for example, in U.S. Pat. No. 8,180,203, with the title Direct Heating Tube and Method of Heating Fluid Using Same, issued to Kurano on May 15, 2012, the contents of which are incorporated herein by reference.

Some embodiments disclosed herein employ a guard column or a retention gap column, to prevent, for example, possible damage to the column coating caused by solvents or to facilitate their removal from the column. Generally, both types of column utilize deactivated fused silica tubing, without a stationary phase, to minimize solute interactions. This tubing can be attached to the front of the column through a suitable union connection.

Typically, guard columns are selected for samples containing non-volatile residues that may contaminate a column, resulting in the non-volatile residues being deposited in the guard column and not in the column. This reduces the interaction between the residues and the sample since the guard column does not retain the solutes (since it contains no stationary phase). Also, Guard columns prevent coating of the stationary phase with residues, mitigating poor peak shapes.

Retention gap columns are used to improve peak shapes in cases such as large volume injections (>2 μL) and solvent-stationary phase polarity mismatch situations in splitless, Megabore direct and on-column injections. Typically, a retention gap column allows liquid or high concentration solvent vapor to move into the column without retention so that the compounds of interest can focus on the head of the GC column. In some cases, benefits of a retention gap are seen when using a guard column.

Specific implementations illustrate advantages over conventional techniques that utilize TDTs. Normally, thermal desorption devices desorb to a secondary trap to further concentrate the sample, with a fairly high flow (10s of mL/min). During that time the sample is many times split. The secondary trap is then desorbed and sent to the GC where it is split again. At 10s of mL/min, the GC will only accept 1 or 2 mL/min. Thus each time a TDT or focusing trap is used, sample is lost due to splitting or just passing through the material (unretained). This is done to make sure the peaks are as narrow as possible, so that a MS can analyze them.

However, the equipment and techniques described herein do not require narrow peaks (since the separation is in the spectral domain and not every molecule is needed), it was found that the TDT can just desorb directly to the GC without focusing and at low flow rates that work with the GC, for instance at 2 mL/min. It was also found that thermal desorption can take place at higher flow rates up to what the column can physically flow when working with semi-volatile organic compounds (SVOCs). While the light material is desorbed and passes through the system, the SVOCs are trapped at the head of the column or Retention gap column until the GC is heated. So the Column acts as the focusing device. Once everything is off the TDT, the flow rate is turned down to normal GC flow rates and the heating of the column is initiated to get the SVOCs off.

In some implementations, the injection port is designed to boil off the solvent or injection gas but condense the rest of the sample within the injection port. This ensures that the only materials passing through GC 12 are the compounds of interest and would be particularly useful when analyzing semi-volatile, near non-volatile species or samples where the solvent is significantly more volatile than the sample and potentially at significantly higher concentrations.

In a design suitable for running extremely large samples, a split/splitless injection port can be modified so that the split is a 100% to the exhaust side until the solvent is exhausted but the less volatile materials are still residing within the injection port. At this point, the mode is switched 100% to the column. See, for example, the injection assembly 80 of FIG. 6, further described below. Known PTV or PVT techniques also can be employed.

Carrier gases that can be employed include nitrogen ($N_2$), for instance ultra high purity (UHP) $N_2$, or another suitable gas or gas mixture, e.g., as known in the art.

Typically output from the separator, e.g., GC 12, is in a gaseous state, containing one or more gases and/or vapors. This output is directed to sample (also referred to herein as gas) cell 14, typically a vessel that can be evacuated and configured to maintain a gas pressure lower than the surrounding (atmospheric or ambient) pressure. In specific implementations, the pressure in the sample cell is within the range of about 0.001 to about 1.0 atm. For instance, a flow rate of 1 mL/minute, a sample cell volume of 200 mL and a starting gas cell pressure of ½ atmosphere can provide a 100 minute time period for data acquisition. This is considered to be a sufficient time window for most GC sample analyses. In one example, a flow rate of about 1.5 mL/min was found to provide an optimum resolution in the case of a 0.53 mm OD column with $N_2$. It was also found that switching to lower pressures may help clear the cell much faster between runs. In illustrative situations, the pressure is lowered to a value within the range of from about 0.1 to about 0.01 atm.

In specific examples, sample cell 14 is heated with a heater 36. This feature is particularly useful when analyzing gases with varying vapor pressures or boiling points, e.g., when measuring semi-volatile or even nearly non-volatile compounds. In examples, the heater 36 for heating sample cell 14 includes but is not limited to heating tape, heating jackets, ovens, Peltier heaters/coolers, cartridge, immersion, and so forth. A survey of many compounds, including compounds that boil at temperatures above 300° C. showed no condensation with a gas cell at 191° C. or 375 F. IR optics and spectrometers work better at lower temperatures. Lightpipes are routinely kept at 300° C., due (at least in part) to the higher concentrations found in the lightpipe.

The pressure in the sample cell is reduced with the help of vacuum pump 18, e.g., a traditional foreline oil pump, a diaphragm pump or another suitable pump or alternative apparatus capable of drawing a vacuum. The pressure in the sample cell can be monitored with a sensor, such as, for instance, absolute pressure sensor 20.

In some cases, no vacuum is required and the system can be operated at a suitable pressure. For instance, a compressor or column head pressure could be used to compress the output from the GC into the sample cell 14. Preferably, over pressurizing is avoided.

Sample cell 14 also receives electromagnetic radiation, for instance from light generated in FTIR arrangement 16 and can be designed to fit in the sample compartment of a commercial FTIR or other type of spectrometer. The cell is provided with optical components, such as, for example, windows, that allow transmission of an electromagnetic radiation beam within a desired wavelength (or frequency) range. Examples of suitable materials that can transmit IR include potassium bromide (KBr), potassium chloride (KCl), cesium iodide (CsI), barium fluoride ($BaF_2$), sodium chloride (NaCl), calcium fluoride ($CaF_2$), magnesium fluoride ($MgF_2$), zinc selenide (ZnSe), zinc sulfide (ZnS), thallium bromoiodide (KRS-5), silver chloride (AgCl), silver bromide (AgBr), lithium fluoride (LiF), sapphire, diamond, silicon, germanium, fused silica, AMTIR-1 ($Ge_{33}AS_{12}Se_{55}$) and various silicon, cadmium, selenium and germanium based glasses and many others, as known in the art.

Sample cell 14 can be configured for multiple-path (also known as multiple-pass or long path) absorption. As seen, for instance, in FIG. 2B, reflector 30A directs the electromagnetic beam from a source, e.g., FTIR arrangement 16, to sample cell 14, configured for multiple pass absorption, indicated by the arrows. By increasing the path length traveled, multiple-pass arrangements can be used to measure low concentration components or to observe weak absorption spectral features without increasing the physical length or volume of the cell itself. Since the detection limit of the system is directly related to the volume/path length ratio, decreasing the volume or increasing the path length lowers the concentrations that can be detected. Assuming no signal losses, doubling the path length or reducing the volume in half will lower the MDL by a factor of 2.

Normally, multi pass cells do not utilize extreme reflections due to losses not from the mirrors or their coatings but because of contamination from the sample. A gas emerging from a GC, however, is fairly clean and relatively free from particulate matter. In addition or alternatively, contaminants can be controlled in cells configured to be sealed or nearly sealed, and never opened. While any suitable material can be utilized to form the cell seals, metal seals provide the added advantage of circumventing small atmospheric leaks or "virtual" leaks or bleed from the O-ring materials. Based on the low level of contamination encountered in the embodiments described herein, the cell can be designed with significantly more passes through a similar volume and base path length. The optical throughput of the cell can then be calculated by the reflectivity to the order of passes (i.e., $0.995^{128}$=0.526 or nearly 53% transmission). In comparison, a gas cell at 32 passes and 0.985 reflectivity is about 0.6 (60% transmission) or 4 times less sensitive.

In some cases, existing light pipe technology quotes 5 ng detection for very strong absorbers. While having a concentrated sample into the analyzer is advantageous, conventional cells suffer from typically short path lengths and losses in the light reaching the detector. Designs such as described herein can result in 10 to 25 times better SNR once the sample cell path length to volume ratio is optimized.

In certain embodiments, longer path lengths are used in combination with higher reflective coatings like enhanced silver, yielding a reflectivity in the 0.992 to 0.995 range or greater. Coating optimizations, in the IR region, for example, could further improve reflectivity, e.g., by a factor or 4 to 8 or even more.

Thus several factors can be important in optimizing the sample cell design. Considering the path length to volume ratio, many FTIR gas analyzers with a 5 meter (m) path have a volume that is 10 times larger, making the peaks 10 times smaller. The ultimate sensitivity will be achieved when the longest path length possible is attained, while maintaining the gas cell at 200 mL or smaller. This will be based on reflectivity and aberrations due to cutting the mirror surface. 128 to 256 passes should be possible with known coatings. 1,000 passes might be possible based on Cavity Ring-Down techniques and laser technology where reflectivity can be 0.999 or greater, which can be implemented in other embodiments. Compared to a sample (gas) cell having 32 passes and providing 5 m (such as one of the sample cells used to demonstrate aspects of the invention), a gas cell with 128 passes would produce absorptions 4 times higher. With a high reflectivity mirror coating there would be no significant loss in throughput. At a theoretical 0.999, 1000 passes could be used, with only a 50% loss in signal. That would generate 31 times the absorption of the 5 m cell and 15.5× lower MDL.

Figure 3:
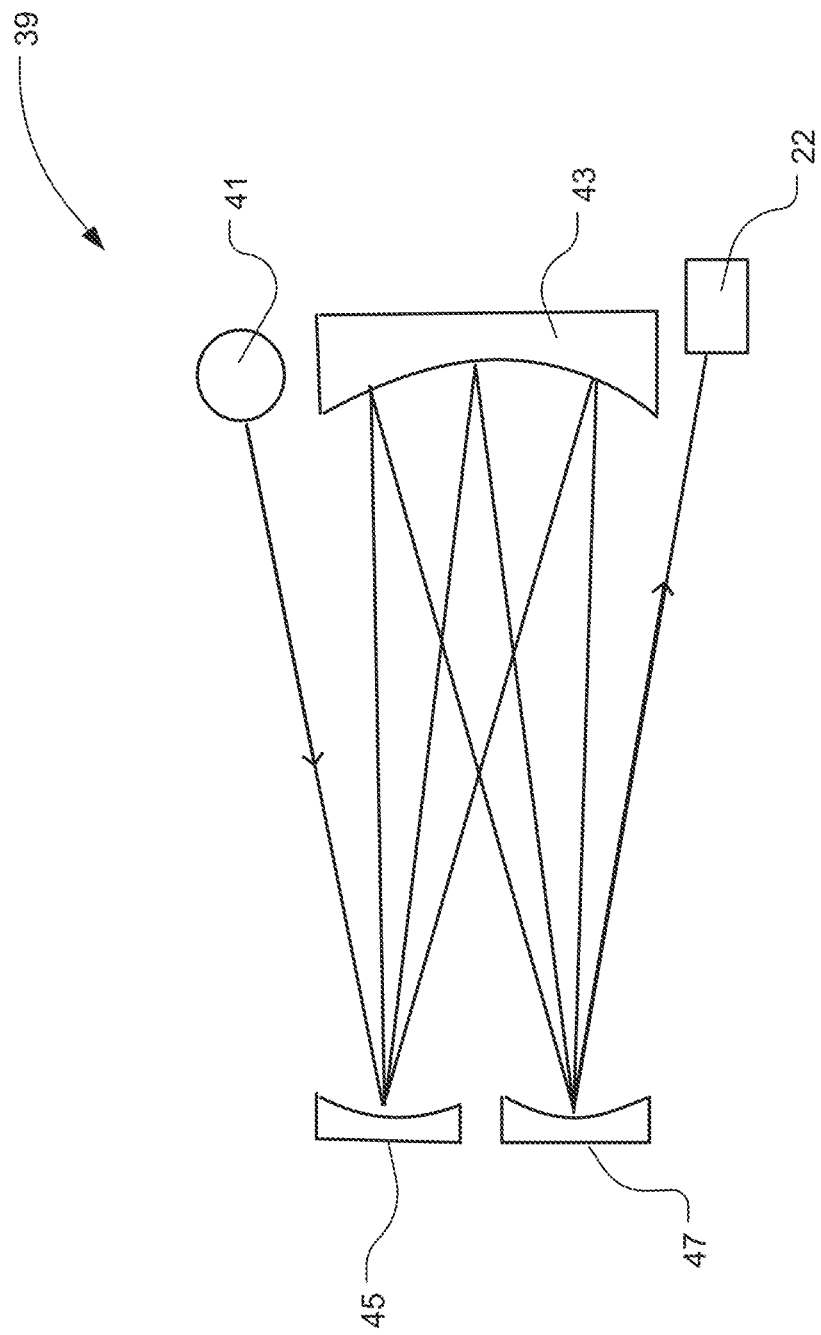
FIG. 3 is an illustrative schematic diagram of a White cell arrangement.

In specific implementations, sample cell 14 can be configured as a "White cell" type. The principles of a traditional White cell arrangement, employing three spherical concave mirrors having the same radius of curvature, are illustrated in FIG. 3. Shown in this figure is White cell 39, including light source 41 and concave reflectors 43, 45 and 47. As seen in this schematic diagram, a light beam generated by the light source or a spectrometer, photometer or interferometer is reflected between reflector 43 and reflectors 45 and 47, exits the optical configuration defined by the three reflectors and is directed to detector 22. While the position of the input and output beams remains unchanged, the number of traversals can be varied by slight rotations to either element 45 or 47. Generally, the total number of traversals in a White cell is a multiple of 4.

Second generation multiple-path gas cells can use non-spherical concave mirrors to improve image quality and optical throughput. Some second generation designs have mirrors (such as mirrors 45 and 47) cut onto a single metal or glass blank (see, e.g., FIG. 2B, element 14). This provides a fixed path length and the mirrors can be the solid end caps of the gas cell allowing for smaller sample cells that are easier to align.

In specific examples, the modified White cell employed in system 10 is a fixed path cell, with no adjustment for path length. Such a design reduces the number of variables to be monitored and/or controlled. In one instance, the White type cell has a volume of ~200 mL. Using gold mirrors can produce a path length of about 5.11 meters (m), while enhanced silver mirrors can result in a path lengths of 10 m or much longer. This increase in path length and change from gold to silver improves the throughput of the gas cell and provides an approximate doubling or more of the absorption signal which further reduces the analyte MDLs.

In many implementations, the White cell utilized, e.g., a second generation White cell, is heated, for example to a temperature such as 150° C., 200° C., 250° C., 300° C. or higher, facilitating the use of the gas cell to analyze samples with varying vapor pressures or boiling points, e.g., to measure semi-volatile or even nearly non-volatile compounds. As described above, suitable heating means include but are not limited to heating tape, heating jackets, ovens, Peltier heaters, cartridge heaters, immersion heaters, and so forth.

Other multiple pass cell designs can be utilized. Examples include but are not limited to Herriott cells, Pfund cells, cavity-ring down cells, and integrating spheres.

Referring back to FIGS. 2A and 2B, output radiation exits sample cell 14 and is directed by reflector 32 to detector 22, for instance a MCT device suitable for measuring the light in an FTIR. Specific examples employ liquid nitrogen ($LN_2$) cooled MCTs. A suitable detector for a broad spectral analysis capability can be a 1 mm mid-band MCT with a cutoff of 16 μm. 0.25 mm to 0.5 mm mid band detectors, 22 to 16 μm detector cutoffs also can be used, typically for broad analysis, while 7 to 5 μm detector cutoffs can be selected for more specialized analyses to even lower MDLs. Numerous other detectors could be utilized but not limited to, such as InSb, InSb/MCT two color detectors, silicon, InGaAs, AlInGaAs, PbS, PbSe, Ge, TGS, DTGS, LiTaO3. Different cooling technologies can be utilized for the detectors such as TE (Peltier), Stirling, $LN_2$, and liquid He.

A very narrow band MCT detector can be employed in some situations, offering about an order of magnitude improvements in sensitivity. Currently, very narrow band MCT detectors are only operational in the 1-5 μm range. This range covers the C—H and O—H stretching region. While hydrocarbon identification is typically based on the 5-20 μm fingerprint region, there appears to be enough variation along with GC separation to make feasible hydrocarbon specification using the 1-5 μm range, at least for some applications. As an added advantage, very narrow band MCT detectors can run thermoelectrically- or TE-cooled as compared to $LN_2$ cooled.

$LN_2$ is not always required with other types of detectors, e.g., if DTGS (deuterated triglycine sulfate) detectors are employed, for continuous operation, for example.

The system can be provided with one or more valves. For the IR exhaust interface, for example, one or more valves 24 can be disposed between pump 18 and the exhaust of sample cell 14. The valve system can fully open the sample cell to the vacuum pump or can open and close to moderate the sample cell pressure to a desired level. Fluid flow out of the sample cell can be monitored and/or adjusted, for example with a mass flow controller.

One or more additional valves can be included at the GC-FTIR interface. For example, system 10 can include a heated two directional valve, shown in FIG. 2B as elements 26A and 26B, one direction going to the IR and the other to a bypass to a vacuum pump. In specific examples, both the sample cell and bypass are held at the same low pump pressure. Including such a directional valve could allow for solvent or injection rejection as it elutes from the separation device, the possibility for very large sample injections, mega-bore columns or large packed columns (while still making possible low parts per trillion (ppt) detection levels), removal of volatile organic compounds (VOCs) from semi volatile organic compounds (SVOCs) analyses, and so forth.

In another possible operating mode, directional valve 26a is opened for short periods by the computer system 34 to release a slug of effluent from the GC to the gas cell and then closed again, thus maintaining a constant concentration in each run. It also can give a constant background for comparison purposes. This approach can reduce the size of the data set since the only spectra gathered are collected after a slug of gases are added. In this mode, a 60 minute run could translate into 60 points or 120 points or some other number. Valve 26a can be designed and/or optimized to prevent leakage when heated. In one implementation, the directional valve 26a is implemented as a mass flow controller that controls the flow of effluent from the separator 12 e.g., GC 12, into the gas cell 14.

System 10 can include electronics, computer systems, video displays, devices, units, interfaces and/or other components for data processing, analysis (including multivariate qualitative and quantitative), recording, reporting, equipment controls, automation, flow control and controllers, pressure sensors and controllers, heaters and temperature controllers, valves and vacuum generation technology, spectral libraries, and so forth. These components are generated indicated by reference 34.

During operation, gas is captured in sample cell 14 for a specific time, based on the gas turnover rate in the sample cell. Various flow conditions can be employed. In a transient mode, for instance, the entire experiment (run) is conducted under a set, i.e., unchanging pressure, e.g., under a set vacuum pressure. In a full integration mode, sample cell 14 is evacuated and the sample is allowed to accumulate in the sample cell, with the pressure changing throughout the analysis. Also possible is a partial integration mode, where the sample cell is evacuated to a set pressure and a dilution gas is added and maintained in the cell for a period of time, e.g., 1 minute. Other operating modes can be employed, such as, for example, a mode that reduces the size of the data set, as described above.

In some arrangements, a continuous carrier gas flow of $N_2$ (or other carrier gas) is directed from GC 12, into the sample cell. If desired, sample cell 14 can be closed to the $N_2$ flow from GC 12, for a given time interval. In yet other arrangements, the carrier gas, e.g., $N_2$, or the sample from the GC can be diverted to a secondary pumping service (not shown in FIG. 2B) to prevent spectral interference from large concentration compounds such as solvent species. The flow can then be switched for sample collection. If pumping continues, the compounds that come off during this time will be standard chromatographic components (peaks) and their concentrations can be calculated as such. The peak will go up and go down as it enters and exits the sample cell so no further averaging will be done.

If sample cell 14 is initially evacuated, then sealed from pump 18, the carrier gas and sample components from the GC can accumulate in the sample cell and spectra can be obtained during the entire data collection. Since the chemicals are captured in the sample cell, the entire amount of each gas (compound) can be measured once it has completely eluted from the separation device (GC). Since the gas cell is a multiple pass gas cell in a preferred embodiment, there can be an increased absorption for each gas when compared to "light pipe" system in an optimized design. By letting all the gas remain in the gas cell, this in effect integrates the sample peak from a traditional analyzer where the sample moves past or through the detection system. This integration provides a further enhancement in SNR, which can be a factor of 2 to 5 times since the entire amount of sample is measured once it has completely eluted. Typically, this improvement is dependent on the width of the eluted peak. Narrow peaks will have less of an enhancement than late eluting compounds that may be a minute in length or longer. But this is another advantage of this technology since sensitivity is not lost by having late eluting compounds that spread out in time. Also, since the analysis is looking at the integration of the peak, many subsequent spectra can be co-added to further reduce the noise level and improve the detection limits. Increasing from 1 sec of data collection to 60 sec can improve the SNR by nearly a factor of 8. So, the aforementioned enhancements may improve the SNR or MDLs relative to some of the current "light pipe" designs.

To improve the analysis/analyzer specificity, the background spectrum will change with time. Initial background spectra will be acquired prior to sample elution then as time goes on; the background spectrum will be created from previous sample spectra (average of sample spectra) collected prior to the current sample spectra and compound elution. By moving the background spectrum in time, all compounds in the gas cell prior to the current background no longer will exhibit spectral features in the absorbance spectrum. The closer in time between this dynamic background and the current spectra, the more reduced the chance that any previously eluted compounds will affect the current measurement. This moving background will allow for the measurement of trace compounds in the presence of very high concentrations as long as the compounds are separated in time. The time separation between the sample and background points could be constant or variable, depending on the width of the eluted peak. If long separation times are required for an analysis, both the separation between the two spectra could increase with time.

In a specific approach, solvent that comes through can be let to bleed to the pump. The lower the pressure the better the reduction of the solvent. Preferably, while the vacuum is open, the background does not move, since at some point the background could have higher concentration levels than the sample. Potentially, gases contained in the background spectrum being pulled out of sample gas cell could give rise to negative peaks. To avoid negative peaks and render interpretation of the data more user friendly, one could chose to forgo a moving background while the sample cell is pulled by a vacuum.

The amount of averaging for background and sample spectral file can be application dependent, for instance 1 min. The averaging could be increased as the chromatography gets longer since the peaks will be broader and require more time to enter the cell further improving the SNR or MDLs. Increasing the averaging and the skip time as time goes on can generate better detection limits for later or latest eluters (that normally show the worst detection limits). Since each resultant compound feature will be a peak with a flat to near flat top, the resultant top could be further averaged to wring out another enhancement of the SNR or MDL.

In many instances, the full integration approach produces the lowest MDLs. With proper detector and optical optimization, sub nanogram (ng) to 1 ng quantities can be qualitatively and quantitatively measured by FTIR for volatile, semi-volatile and near non-volatile compounds directly. Experiments routinely demonstrate 0.5 to 5 ng absolute sensitivity and lower (e.g., 10 to 25 times lower) levels could be possible with an optimized sample cell. Since large samples can now be provided to the instrument without damage to the analyzer and since samples are in many cases already concentrated, this technology will be able to measure in the parts per trillion range or lower from the original sample. Using thermal desorption tubes (TDTs), the techniques and equipment described herein, can detect single digit ppt levels of semi-volatile VOCs or SVOCs. With further optimization, detection limits are expected to reach the ppq range for these types of materials.

The carrier gas flow can be interrupted for stop-flow measuring. In some instances this may require user monitoring, e.g., by the operator. It is believed that this approach presents particular benefits for the full integration mode, since even longer averages of spectra can be obtained. In one example, the flow into the sample cell is stopped, while the column flow continues. At specified intervals, e.g., every 30 or 60 seconds, the valve opens briefly, for 10 seconds, for example, to dump the next plug of gas into the sample cell.

In another approach, stopping the flow of carrier gas is also possible, using a suitable arrangement.

For mixtures that include solvents, the solvent may be vented before the separation device, after the separation device or allowed to flow through the sample cell. In a semi-volatile analysis, for instance, volatile species come off first and could be either diverted at a specially configured injection port or after the separation device from the sample cell, or the sample cell could be maintained under vacuum removing the volatiles into the vacuum system until it is desired to measure for semi-volatiles. PVT or PTV devices also could be employed.

In some embodiments, the sample is concentrated to obtain determinations to low parts per trillion or high parts per quadrillion levels. For semi-volatile or near non-volatile materials (e.g., pesticides, herbicides, dioxins, explosives, nicotine, mold, mold sources, and so forth) MDLs could be in the parts per quadrillion (PPQ) range. Measuring in the parts per quadrillion range can allow detection of nearly any semi-volatile chemical in a sample.

Suitable concentration techniques include, for example, those based on thermal desorption tubes (TDTs), purge and trap, solvent concentration approaches and others. A TDT AirScan® system, for instance, relies on a multi-matrix sorption tube developed by Prism Analytical Technologies, Inc., U.S.A., that is designed to trap a wide range of compounds (both polar and non-polar) from the air. After sampling, the sorption tube can be submitted for qualitative and quantitative identification of over 400+ compounds.

In some cases, a TDT used to collect VOCs or SVOCs could be run for longer periods of time to significantly concentrate semi-volatiles. For instance, if a sample cell is 200 mL in volume, the amount of air concentrated can determine the concentration capability. For example, collecting 24 hours of air at 200 mL/minute (min) would result in a 1440 fold concentration. Since volatiles can move on and off the TDTs, they are not expected to overly concentrate and low ppt or even ppq levels may be possible for semi-volatile compounds. This would now allow for a direct ambient air measurement of materials that are normally monitored using collected dust samples (solvent extracted, concentrated then injected) which are notoriously inhomogeneous and can provide very biased results. If this GC-FTIR technology has a base sensitivity of 1 ng for a pesticide (or any semi-volatile), taking a sample with a 1440 fold enhancement would potentially allow for approximately 3.5 pg/L of a pesticide or herbicide or similarly low volatility compound to be detected. For a compound with a molecular weight of 250 g/mol, the detection limit would be approximately 500 parts per quadrillion (ppq). Potentially, both numbers could be lowered, e.g., by a factor of 2.5, with a sampler running at 500 mL/minute, or potentially higher.

Various steps in the method described herein can be conducted manually. In specific embodiments, at least one and preferably more or even all activities are automated and performed by the computer system 34 that can be connected to or integrated with system 10 or one or more of its components. In specific implementations, the computer system 34 is connected to or integrated with at least one of the FTIR spectrometer, the GC and the FTIR detector being employed. Computer system 34 monitors and/or controls the pressure in the sample cell 14. It preferably controls the operation of the vacuum pump 18 and various valves 24, 26A, 26B. The computer system 34 further preferably monitors the pressure detected by the pressure sensor 20 and/or the output of other sensors/transducers. In specific examples, the computer system 34 accesses internal or external libraries, and/or other devices or sources needed for data collection and analysis. In the embodiments of FIGS. 2A and 2B, for example, computer system 34 controls the operation of the GC 12 and receives the spectral information generated by the FTIR 16. The computer system 34 further controls the operation of the vacuum pump 18 and receives information from the pressure sensor 20 and detector 22. In other embodiments, computer system 34 controls valves 24, 26A and 26B.

Specific aspects of the invention utilize sample handling, detection/monitoring devices, and controls operated by the computer system, software executed by the computer system, and libraries and other information stored on the computer system, and so forth in order to execute at least some of the following functions:
- monitoring retention times (RT) of GC;
- evacuating the gas cell to a specific vacuum pressure and optionally sealing it;
- determining what vacuum is needed to gather all gas into the gas cell without pressurizing the cell and affecting GC;
- measuring in absolute mode so the gas cell pressure does not affect the resulting measurement;
- coupling the GC exhaust to the FTIR gas cell directly;
- monitoring the pressure of the gas cell intermittently or, preferably, continuously;
- integrating the peak signal, thus providing significant SNR improvements over current technology;
- averaging each peak by measuring the compound repeatedly after it stops coming off the GC;
- managing FTIR spectral data to control the output data stream;
- determining which of the data obtained are sample data and which are to be used as background data;
- determining how long a compound can be analyzed before interferences occur rendering the measurements unreliable;
- database searching for compounds as they come off;
- quantifying compounds as they come off;
- correcting for concentrations with the help of internal standards;
- generating calibration files for each compound;
- developing procedures (protocols) for analyzing data as compounds are coming off to correct for interferences;
- determining when a new compound is eluting from the GC;
- determining when the compound is finished emerging from the GC;
- determining for how long a compound can be quantified after it comes off the GC, e.g., using errors related to the measurement;
- running multiple analyses simultaneously for different compounds;
- running multiple analyses for each compound to determine best result;
- varying the spectral regions utilized based on potential interferences;
- predicting MDLs as measurements are being taken;
- determining retention time and/or retention index for future analyses or set analyses.

Steps shown above can be repeated one or more times.

Specific embodiments utilize various detectors, actuators, hardware, software interfaces, heaters, coolers, vacuum pumps and flow control, mirror movements, sample handling or other means, or combinations thereof, to provide instrumentation control. Elements and/or features that can be controlled automatically include but are not limited to parameters characterizing the gas flow in and (eventually) out of the sample cell, the carrier gas flow, valve openings and closings, pump operation, pressure levels, sample injection, sample concentration techniques or devices such as TDT's, traps, purge systems, spargers and so forth (if such techniques or devices are utilized) and others.

In specific implementations, a control circuit managed by the computer system 34 dynamically controls the sample cell pressure. For instance, automated valves can be set to pull a vacuum on sample cell 14 before starting a run. Pressure levels in the cell can be controlled automatically as well. In many cases, isolating sample cell 14 from pump 18, thus allowing gas to accumulate in the sample cell, also is performed automatically. Automation can be utilized to set a desired carrier gas flow of $N_2$ (or other carrier gas) from the separator, e.g., GC 12, into the sample cell, to isolate the cell from the carrier gas, to divert the carrier gas to any secondary pumping station, to switch the flow to the FTIR gas cell for sample collection, and so forth.

Figure 2B:
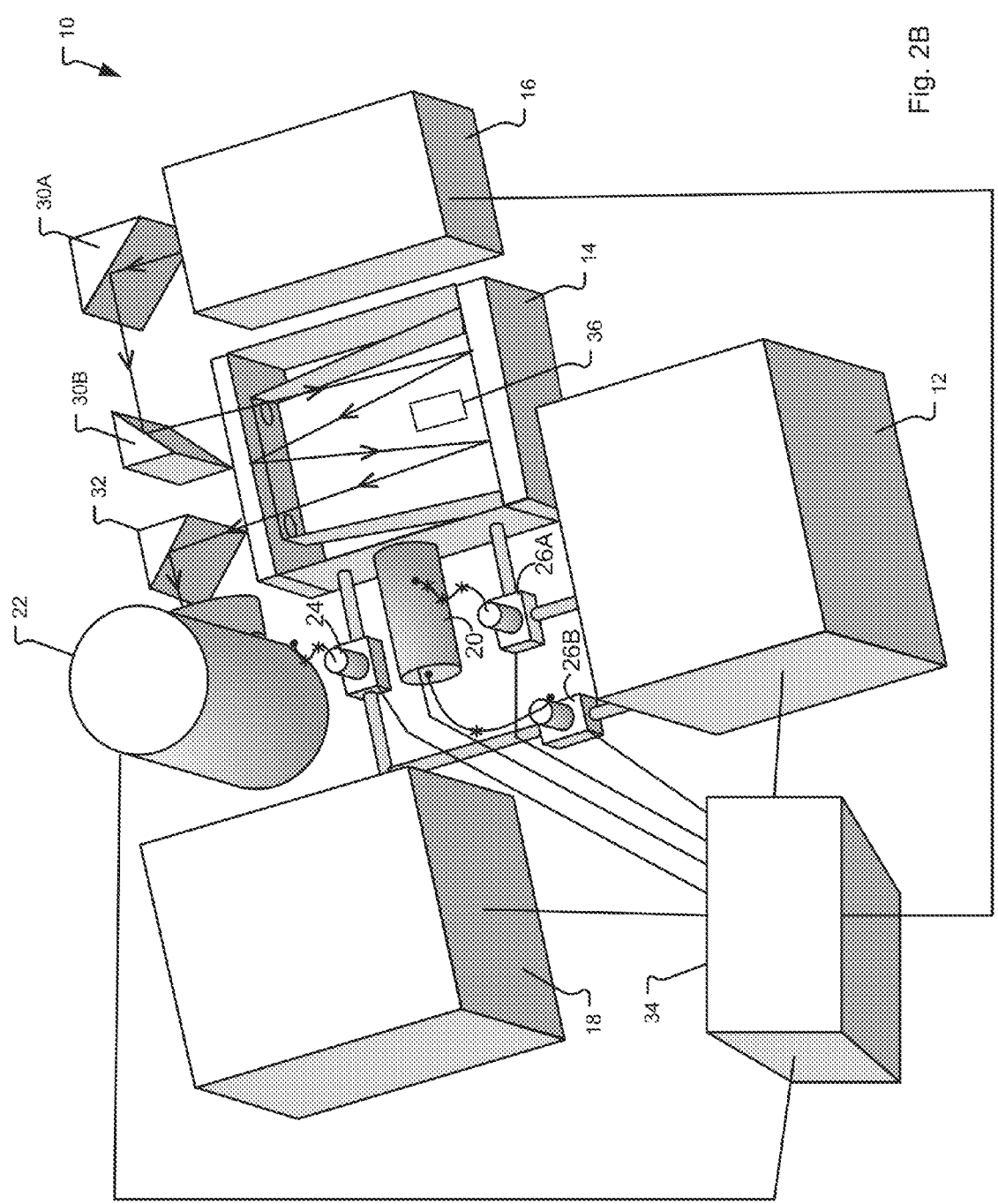

With respect to data handling (e.g., data collection and analysis), a process carried out in a system such as, for example, system 10 of FIG. 2B can involve: data collection; data integral/differentiation/signal averaging, data spectral deconvolution/quantification; data reporting; and others. Each function can be controlled through methods such as further described below.

In one example, a suitable configuration for data collection has a resolution (with cosine apodization) of 4.0 cm$^{-1}$. As known in the art, apodization can be used to change the shape of a mathematical function, an optical transmission or a mechanical structure. In the system and method described herein, apodization is particularly important for obtaining spectra without artifacts when very low noise spectra are desired. For example, an apodization function that goes to zero appears to make a significant difference in baseline artifacts. Valuable information also can be obtained using higher or lower resolutions. In some cases, protocols are used for calibrations that are stable from instrument to instrument or over time. For instance, constant calibration of the detector can be implemented with a suitable detector linearization algorithm.

An illustrative configuration has about 34 co-added scans that can take about 5 seconds. Sampling time could be shorter or longer depending on the separation technology utilized. In some cases, better resolution of the data is obtained using shorter time periods, 2 seconds, for example.

Even with data averaging, the peaks appear narrower and somewhat better resolved. So a default or initial run can be conducted 1 to 2 seconds.

Calibration data can be provided for each compound, and, in specific implementations at multiple concentrations. Retention index per compound can be determined using hydrocarbon reference standards or utilized from current mass spectral library data. For instance, retention index data are available from many sources, as known in the art, and are typically provided based on the type of column being utilized. Calibration data can be called when a certain index is reached, e.g., for the deconvolution described below. An initial prediction could be performed to determine which compounds within a retention index window might actually be present. This initial screening will limit the number of compounds then utilized in the multivariate analysis.

Data integral/differentiation/signal averaging functions can utilize, for instance, a 1 minute moving spectral average. Time spacing between background and sample spectrum can be varied.

Data spectral deconvolution/quantification can be provided by a moving multiple linear regression based on compound retention index. A new regression matrix can be built for each spectrum analyzed in real time. Compounds selected for each regression are present for a relative distance +/− of its own retention index. Very high concentration components, internal standards or solvents can be present in a select set or in all regressions.

Multiple region analysis for optimal fit and analysis can be employed. For example, software can be designed to select one, more or all absorption regions present in an IR spectrum for optimized analysis and precision. In specific examples, the software is set to manually select all the compounds to be analyzed and their respective analysis regions to be used.

Data reporting can include information such as compounds identification, compound retention index, compound retention time, level of sample concentration, original concentrations of sample (before concentration), "goodness" of fit of spectral match.

In many implementations, data analysis is conducted during the data collection process. In specific examples, the process includes one, more or all of the features described below.

The process can begin with evacuation of sample cell 14 to a specific pressure, e.g., a pressure selected from the range of from about 0.001 atm to about 0.8 atm. A typical transducer utilized can measure up to 1.3 atm. $N_2$ can be used as the fill or carrier gas.

Standard drivers for the spectrometer's computer system can be utilized during spectra collection, a process that typically includes obtaining a background spectrum. In many cases, this background spectrum is an average of spectra determined by the computer system for ~1 and 2 minutes.

IR spectra will then be collected by the computer system at a nominal spacing, for example, every 5 seconds. While the spacing could change during the experiment, this is not necessary since the data will be averaged after collection by the computer system. Typically, therefore, spectra can be collected at the same spacing from beginning to the end of the sampling, with 2 seconds providing good resolution in many cases.

Again, each reported spectrum will be an average of IR spectra over that time frame. While the same number of data points will be present, after the initial few data sets they will be averaged spectra determined by the computer system. Averaging can take place in Igram, Single Beam or Absorbance space and comparisons can be undertaken to determine which results in the best SNR by the computer system. A single beam spectrum reduces computational requirements by not needing a FFT (fast Fourier transform) to occur each time, thus providing more time for the quantitative algorithm to be developed and utilized.

The average time used can be determined based on the speed of the chromatography, separation or distillation either automatically by the computer system or by an operator. In many cases tests can be conducted using 1 minute averages. Other time periods can be employed. For instance, the averaging time could be shorter for faster chromatography and could be set by the user or based on the time length of data. As the chromatography gets longer, the peaks may exceed 1 to 2 minutes in length and longer averaging times might occur, determined by retention time or some other factor like retention index or by analysis of the data by the computer system.

If the data are collected by a FTIR, the raw interferograms will be saved by the computer system as well, since the interferograms can allow for additional processing of the data without loss of SNR. To reduce the need for redoing the FFT, the single beams can be saved as well.

The resolution can be anywhere from 0.25 $cm^{-1}$ to 32 $cm^{-1}$. A smaller range is 2 $cm^{-1}$ to 8 $cm^{-1}$ is used in some examples. Currently, about a 4 $cm^{-1}$ resolution, for example, appears to balance the need to separate similar compounds, while achieving high SNR.

Once the spectral averages are generated by the computer system, ratios between the initial minute or two of data against the original background can be obtained. The resulting absorbance spectrum can be analyzed by deconvolution software executing on the computer system. To avoid complications associated with negative peaks, the moving background is not started until the sample cell is closed and the sample begins to integrate.

After some point (e.g., 1 to 2 minutes into the data collection) the background will begin to move with the sample and a new background can be used against a new sample spectrum to generate the sample absorbance spectrum by the computer system. The separation of the background and sample will then be in time, a time that could be fixed at 1 to 2 minutes or can be varied with the length of data collection.

In a case in which a peak is 3 minutes wide, the computer system uses a background that is more than 3 minutes prior to the end of the peak in the original chromatograph. Thus the chromatography, separation or distillation will most likely determine the spacing between the background and sample.

In this procedure any compounds that are present in the current (moving) background will be eliminated from the data by the computer system. Thus, compounds that enter the sample cell before the background will be zeroed out, as will compounds that come in during the background. Only compounds that come into the sample cell after the background will show up in the resultant absorbance spectrum that is calculated by the computer system. This simplifies the deconvolution data analysis algorithm executed by the computer system since the algorithm only needs to analyze the compounds that could be present at that time.

The relationship between the degree to which the separator resolves the species in time (for instance the length in time of the GC peaks) and the period used to calculate background spectra can be determined in various ways.

In many cases the background is considered to be at least 1 to 2 minutes in length. Thus at the beginning of starting the carrier gas or for the evacuated gas cell the background will last until some point in the future. Since spectra are stored every few seconds by the computer system, steps performed manually or automatically can be redone with a different set of parameters after the data are fully collected. So, the software executing on the computer system, the operator or both have many opportunities to optimize the results.

In one approach, raw data can be collected to determine the time period required for large compounds to elute at each point in time. This can also be accomplished by relying on internal or external standards. The data collected provides information about the chromatography going forward. So, at retention index (RI) 300, one setting for the background, another skip, then sample spectra, at RI 400 another and so on. Since the raw data already exists and the large peaks show up as integrated masses, one can check on each data set before, during or after the analysis.

Another approach is completely dynamic, with the software executing on the computer system starting an initial time e.g., 1 minute background, 2 minute skip, 1 minute sample. Then the software performs an optimization. Once the peak gets no taller or reaches a consistent plateau for certain time period, it can be concluded that the correct background and sample integration time have been chosen. This approach is based on actually observing the compound and might also allow for optimization of the background spectrum selection. The closer the background spectrum is in time to the sample spectrum, the fewer interfering species to deal with during the multivariate analysis. This should produce a much better quantitative result.

Yet another approach uses the van Deemter and related equations to predict the width of the peaks moving forward from the internal or external standards. The van Deemter equation relates the resolving power (HETP=height equivalent to a theoretical plate) of a chromatographic column to the various flow and kinetic parameters which cause peak broadening, as follows:

$$HETP = A + \frac{B}{u} + (C_g + C_m) \cdot u$$

where: HETP=height equivalent to a theoretical plate, a measure of the resolving power of the column [m]; A=Eddy-diffusion parameter, related to channeling through a non-ideal packing [m]; B=diffusion coefficient of the eluting particles in the longitudinal direction, resulting in dispersion [$m^2\ s^{-1}$]; C=Resistance to mass transfer coefficient of the analyte between mobile [m] and stationary phase [s]; and u=Linear Velocity [$m\ s^{-1}$].

Other possible options involve using set parameters throughout.

The deconvolution algorithm executed by the computer system is designed to analyze the resultant spectra to determine the chemicals present and their respective concentrations. In specific implementations, each gas to be analyzed has a stored calibration spectrum in the computer system that will be used to identify and quantify its presence. Known IR deconvolution algorithms can be used or adapted. Examples of suitable deconvolution techniques include but are not limited to those based on multiple regression analysis, linear or non-linear regressions, least squares analysis, partial least squares (PLS) analysis, inverse least squares analysis or other approaches.

Most FTIR computer analysis algorithms select several compounds or mixture of compounds to analyze, for example, 2 to 20+ compounds or mixtures. The analysis can involve selecting a region of the spectrum to analyze each gas (where it absorbs). This step can be preset or selected by the computer system based on potential interferences. Multiple regions can be used for each compound to get more quantitative precision and a better qualitative prediction. For example, if a compound has two absorption bands of equal strength where one absorption band is present in the sample spectrum and the other is not, it cannot be the gas in question.

A mathematical matrix or matrices is/are created to analyze for each compound, with some instruments creating just a single matrix and analyzing all the gases simultaneously. Other instruments analyze each compound individually, so that the potential interferences are minimized and such that one compound does not affect the analysis of another. In yet other instruments a compound is analyzed in multiple regions and the results are compared to determine the true presence and concentration.

In many instances, identifying more than 25 compounds from a single spectrum can pose software difficulties. For instance, having 25 unknowns requires 25 independent equations. Often, however, the number of unknowns is considerably reduced by the fact that not every gas absorbs in the same spectral region, with maybe only a few (2 or 3) absorbing at any one spectral location.

Unlike GC-MS, gas phase IR (and, in fact, any optical spectroscopy) absorbance spectra from multiple compounds add linearly to each other. Thus if there are two gases absorbing in the same frequency range, each absorbance is independent or nearly independent of the other and what is obtained is the sum of the two spectra at each frequency.

In specific implementations, the algorithm used by the computer system will be configured to change the compounds being analyzed based on their expected chromatography. Generally, the technique can analyze as many as 25 or so compounds and as few as one. Since components do not need to be completely separated, the GC utilized can be simplified or replaced by less effective separation equipment, for instance by a separator based on distillation principles. Also, since we are quantifying each compound individually the interfering compounds do not necessarily need to be 100% accurate since they are only present in the matrix analysis to help determine the current analyte correct concentration or mass.

If gas chromatograph 12 is replaced by a pseudo distillation apparatus (further described below), the calibration data would have a temperature term added to their library reference file to determine when they would be expected to come off and be analyzed.

During the analysis protocols, each compound can be run against a set of standards to determine its retention index, a parameter usually based on the carbon ladder. For instance, if the compound elutes half way between butane (C4) and pentane (C5), it would have a retention index of 450. In this manner, the retention time can change over time or from instrument to instrument but the compounds will come off at the same relative time to standards in the sample. The retention indices for many compounds can be found in the literature or mass spectral libraries.

Internal standards can be used to set time stamps and/or to ensure that the sample size is consistent. For instance, when a syringe draws up a solution, it can inject not just exactly 1.0 microliter (µL) but also volumes slightly higher or lower, for instance 1.1 µL or 0.9 µL. The internal standards add in known volumes to the sample can improve the accuracy and precision of the measurement by correcting for slight changes in injection volumes.

Figure 12A:
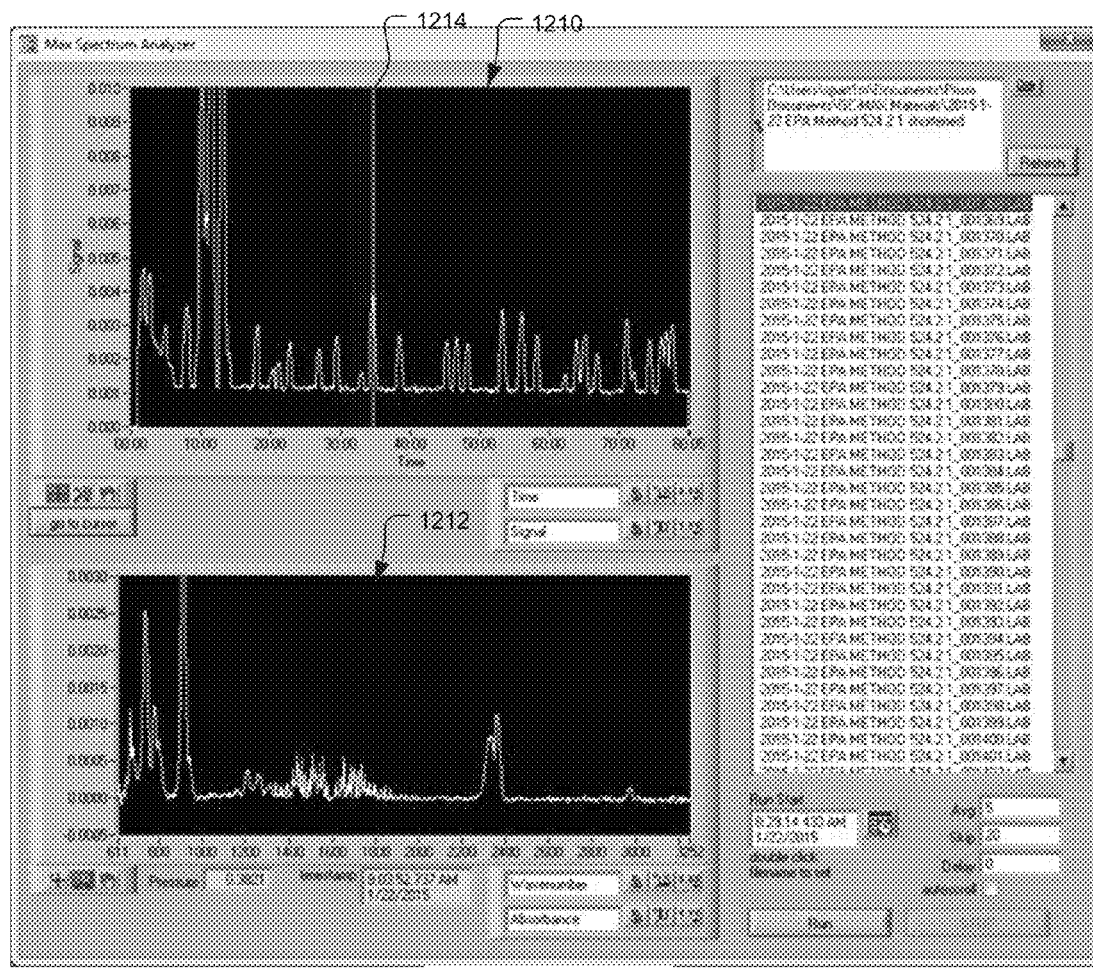
FIGS. 12A and 12B are screen shots of a user interface generated by the computer system 34, in which FIG. 12A includes a top graph 1210 showing is a pseudo chromatogram of peak signal verses time and a bottom graph 1212 showing a spectrum related to the point 1214 in time.

As the chromatography gets to a certain retention index, the compounds that could elute near that time will be added to the prescreening and/or analysis algorithm by the computer system at that point and the number of compounds and the compounds analyzed will be different from point to point in the data. As gases are added and removed, optimizations of the deconvolution might occur. Thus one might measure for a compound in one region with one set of interferences and in another region with other interferences. Once a compound is no longer observed and/or it is outside the retention index window, it would no longer be used in the analysis (unless it is a high concentration component that might vary slightly with time) by the computer system. Since 1 to 2 minute averages of each gas concentration are available, each peak can be at a near constant concentration for this time and the average of that data will be the reported concentration. A pseudo chromatogram can be obtained by just looking at maximum peaks showing up as the compounds come off and plotting that versus time. The plot looks similar to what a chromatographer would normally see. An example for a 60 component mix is presented in FIG. 12A, top graph 1210. This plot shows peaks as a function of run time. It just shows the elution of the compounds from the column. There is no long skip or average on here so the peaks do not flatten out, but the graph would be something a chemist could look at it for compounds. The bottom graph is the spectrum, optical spectral response related to the point in time 1214 (35 minutes). The features between 700 and 1300 cm-1 are from the compound (s) that are peaking here.

Any large concentration compounds found (e.g., solvents that may be present) may stay in the analysis algorithm long past their presence (retention index) just in case the concentration changes slightly. Small changes in large concentration compounds will then be monitored and prevented from interfering with other analyte gases as they elute.

Using the techniques described above, having 50 or so retention index segments and analyzing for 20 compounds per segment, can allow handling 1000 compounds per analysis automatically by the computer system. However, each sample point could be a separate retention index and many compounds may be removed due a prescreening algorithm, so 1000's of compounds could be measured or eliminated during each analysis. Since IR spectra are physical constants, any gas in the IR library can be accurately determined both qualitatively and quantitatively. Since integration is carried out, the chromatography separation is eliminated from the measurement. Thus whether the peak comes off fast or slow, the result is the same as long as the skip time is long enough.

In some implementations, protocols and/or algorithms are designed to correct for pressure broadening. Pressure broadening can be observed in the spectra of some compounds when the pressure changes. Typically, the lighter the molecule, the more pronounced the effect. In one example, the pressure at which a compound is detected is measured by a pressure transducer 20 for the sample cell 14 and is recorded by the computer system. The pressure transducer can be, for instance, pressure sensor 20 in FIGS. 2A and 2B, or another pressure sensing device, not shown in the drawings. Additional spectra can be obtained over a range of pressures. For instance, a first spectrum could be taken by the computer system 34 when the analyte gas is fully present in the sample cell at a low pressure at the onset of the analysis, as the sample cell just begins to fill with gas. Subsequent spectra can then be taken by the computer system 34 at increasingly higher pressures, as the carrier gas accumulates in the sample cell. Similar data can be gathered for other compounds to generate libraries of pressure-related calibration spectra by the computer system 34. The data can then be used correct for pressure broadening effects. For example, it can address uncertainties in the quantitative analysis of very light molecules such as methane ($CH_4$), caused by a varying pressure in the sample cell.

In specific implementations, the temperature of the sample cell will remain constant since temperature variations can affect the absorption spectrum as well.

Once certain compounds are identified and quantified or potentially before spectral analysis as a prescreening technique, a goodness of fit, using, for instance, multiple spectral regions, can be performed to give the likelihood that the peaks observed in the collected spectra are the compound identified or compound in question. Reporting the compound can be accompanied by the percent likelihood that it is indeed the compound as part of the result. In many cases, a 95% or higher may indicate that the compound identified is the correct compound.

Since the resultant data will not be a normal chromatogram (a single continuous line of data containing peaks versus time), reporting software will be very important to understanding the data set. In specific examples, after all the processing, the data can be presented by the computer system as follows. As already mentioned, a pseudo chromatogram using the high points in the spectrum as a function of time is shown in plot 1214 of FIG. 12A.

First, a user selects the gases for which a report is desired (e.g., based on a specific method or EPA requirement). Alternatively, all the compounds found can be selected for the report by an analysis of the entire spectral library.

A limit can be set to decide which compounds are to be presented in the report. If every compound in the library is targeted for analysis, every compound will have a predicted concentration. The average concentration for each compound over the 1 to 2 minute interval will be used for the reported concentration. The limit for reporting (as concentration or ng (mass) level) could be set prior to the analysis as a global level, for each gas in the library depending on the levels at which it is normally seen or it relative toxicity levels.

Figure 12B:
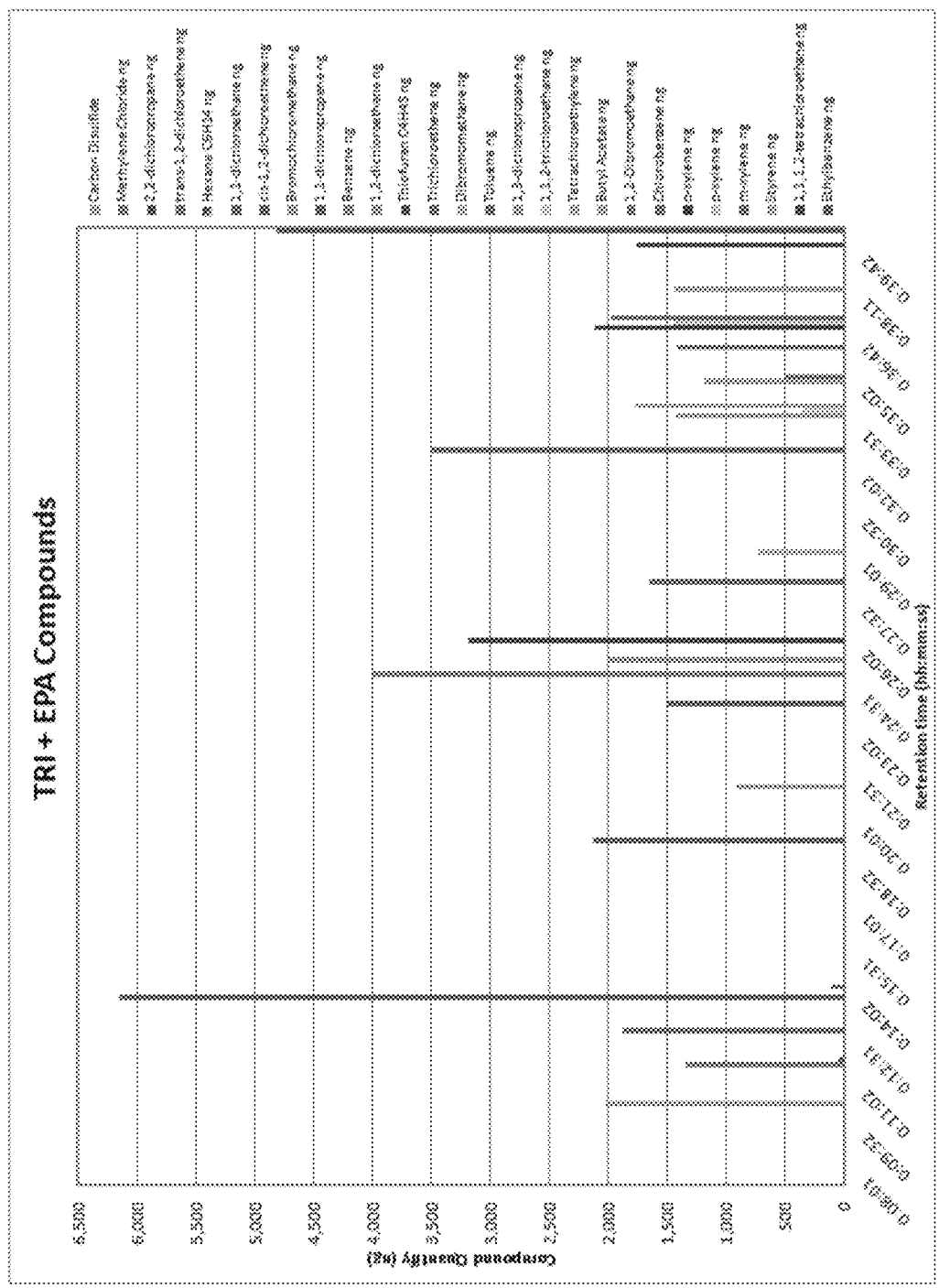

One illustrative reporting pattern includes: retention index, compound name and/or its registration or CAS number, chemical formula, chemical structure, mass or concentration of sample analyzed (ng or ng/L), mass or concentration from original sample (taking into account any further steps to concentrate the sample) and likeliness that the compound is present. If unknowns to the library are found they could be listed by their retention index along with the features identified and likeliness they contain a certain functionality (alcohol, ether, ketone, etc). One illustrative reporting method has mass (ng) or concentration on the y-axis and compounds shown as a single line (bar graph) at their respective R.I. (Retention Index), resulting in a chromatogram that is ng/RI, with the peak having no time length associated with it. An example of this graph is shown in FIG. 12B. Thus the report shows the peak reading in a bar graph form. Unknowns could show up where the R.I. is with an estimate of ng or concentration based on the type of compound present.

The reporting software executing on the computer system can also allow for inspection. For instance an interface can be provided to link a compound listed in a report to the spectra and mathematical matrix used to identify and quantify it. In further implementations, library spectra can be overlaid on the sample spectrum on a video monitor operated by the computer system to show the match. If desired, further software manipulation could remove identified interfering compounds so that only the compound of interest is observed in the spectrum. Data reporting can also include user interfaces generated by the computer system that overlay and/or compare spectral data between a peak feature in a pseudo chromatogram, or any spectral feature at any point in the pseudo chromatogram, and compounds that could be present.

A feature important to many of the embodiments described here is a calibration library maintained by the computer system. With its use, calibrations only need to be collected once by the computer system (for a specific type of FTIR, spectrometer, laser system) and could be integrated with the spectroscopic component used, regardless the type of separator (GC, pseudo distillation, etc.) to which it is connected. A laboratory with multiple "like" instruments could rely on the same calibration, reducing or minimizing the need to calibrate the various instruments.

To obtain the calibration library, each material is measured on a GC with potential columns and stationary phases and compared to standards to determine its retention index. Alternatively, the retention index for each material could be acquired from the literature or mass spectral libraries. All this information once obtained is added to the file for the compound, a file that may further include a reference to boiling point, a temperature reference for distillation purposes, retention index based on column stationary phase type and, if desired, other characteristics of the compound.

Each material is also added to the sample cell at a couple of masses or concentrations (calibration curve) and multiple pressures to correct for pressure broadening effects (if such effects occur). The spectral regions for analysis can be set by the instrument manufacturer, by the user or automatically, e.g., by specific software. Quantification regions can be included, as can other spectral regions in which the compound absorbs, to enable the software to rely on the information for any compound that is using that absorption region for quantification.

A calibration curve can be generated so that a quantitative regression analysis (e.g., linear, quadratic, or, as needed, cubic or quartic) can be performed.

Similar approaches can be developed for transient mode flows or for other flow arrangements that allow the averaging/integration of spectral features taken over a time interval, for instance a window determined by a width of one component in the output emerging from the separator.

Figure 4A:
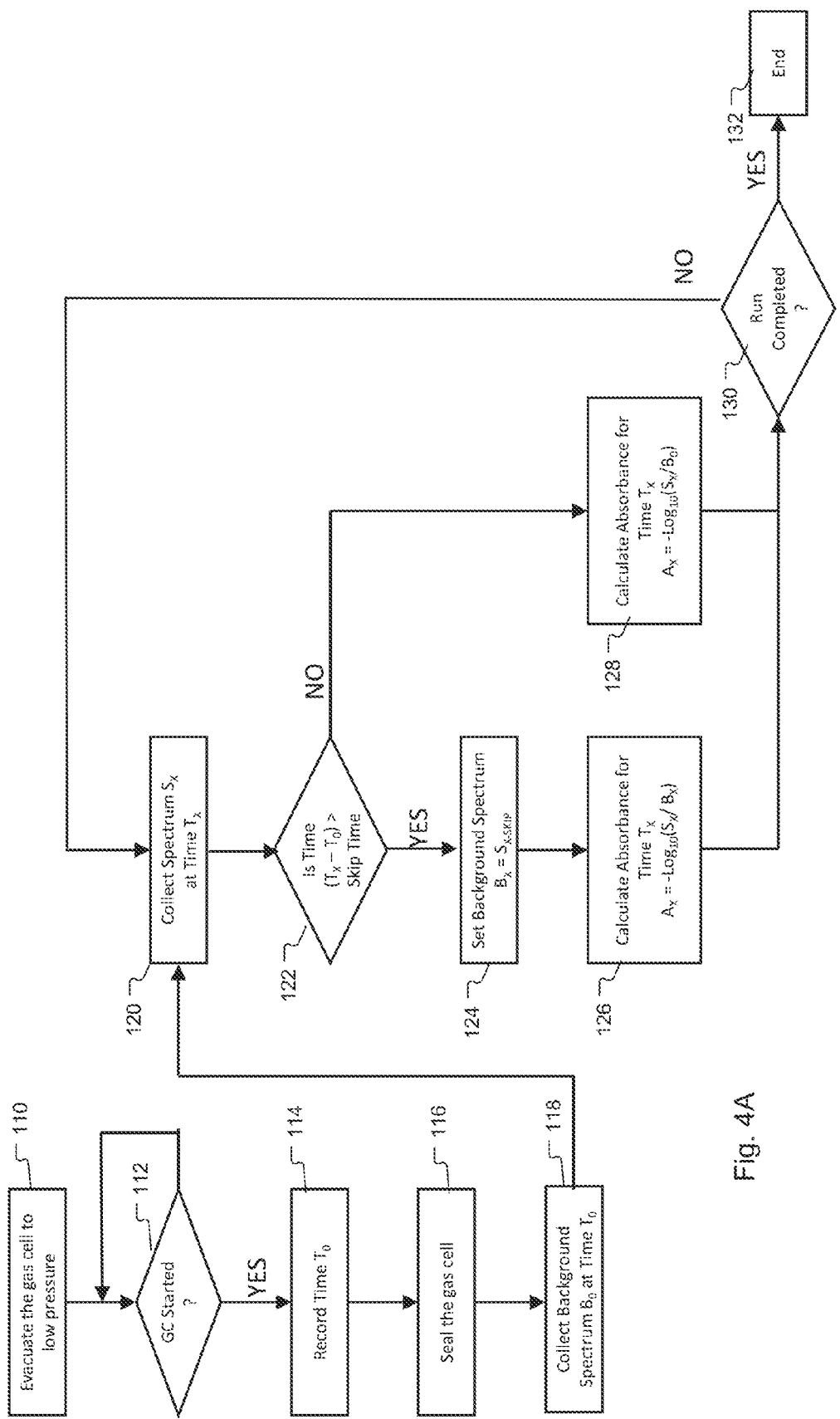
FIG. 4A is a flow diagram illustrating the control of the system 10 by the computer system 34 and determination of component absorbance spectra.

FIG. 4A is a flow diagram illustrating the control of the system 10 by the computer system 34 and specifically how absorbance spectra are determined over the processing run of the separator 12.

Before the separator, e.g. GC, 12 is started, valve 24 is opened and the vacuum pump 18 is operated to evacuate the gas cell 14 to low pressure in step 110. In general, lower pressures in the sample cell 14 produce cleaner background signals, but low pressures are not necessary. In fact, in a different configuration, the output of the separator 12 could be injected into the sample cell 14 under pressure, avoiding the need to draw a vacuum, for example.

Then, in step 112, the computer system 34 waits for the start signal from the separator 12. When start signal from the chromatography system 12, for example, arrives, the start time To is set to the current time in step 114. Additionally, the valve 24 is closed to thereby seal the gas cell 14 in step 116.

Additionally, in step 118, the current single beam spectrum is set as the background single beam spectra $B_0$ for the start time $T_0$.

The system 10 then collects the spectra $S_x$ for the current times $T_x$. These are single beam spectra that are generated by taking the raw interferograms from the FTIR spectrometer 116 and then converting those interferograms to intensity versus wavenumber spectra.

In other situations where a different spectrometer technology is used, the intensity versus wave number spectra might be directly read-out as in the case of a post dispersive system, or simply be a function of the time response of a detector, in the example of a tunable optical source (laser) spectrometer.

In step 122, it is determined whether or not the system has been collecting spectra for longer than Skip Time. Generally, Skip Time may be about 10 seconds to as long as 5 minutes. It is typically between about 20 seconds and 2 minutes, however.

If the difference between the current time $T_x$ and the start time $T_0$ is not greater than the Skip Time then the absorbance spectrum is calculated in step 128. Here, the absorbance spectrum $A_X$ is based on the negative log (base 10) of the current spectrum $S_x$ at the current time $T_x$ divided by the single beam background spectrum $B_0$ detected at the start time. $A_X = -Log_{10}(S_X/B_0)$.

In step 130, the computer system 34 determines whether or not the separator 12 has completed its run. In the situation where it has not, then processing returns back to step 120 and the new current spectra spectrum $S_x$ is obtained for the current time $T_x$.

When the loop has been running for longer than Skip Time as determined in step 122, then the background spectrum is set to the spectrum that was detected previously based on the delay set by Skip Time in step 124. In the example where Skip Time is 60 seconds, then the current background is set to the spectrum that is 60 seconds old. That is $B_X = S_{X-SKIP}$.

Then in step 126, the current absorbance spectrum $A_X$ is calculated as $A_X = -Log_{10}(S_X/B_X)$.

Figure 4B:
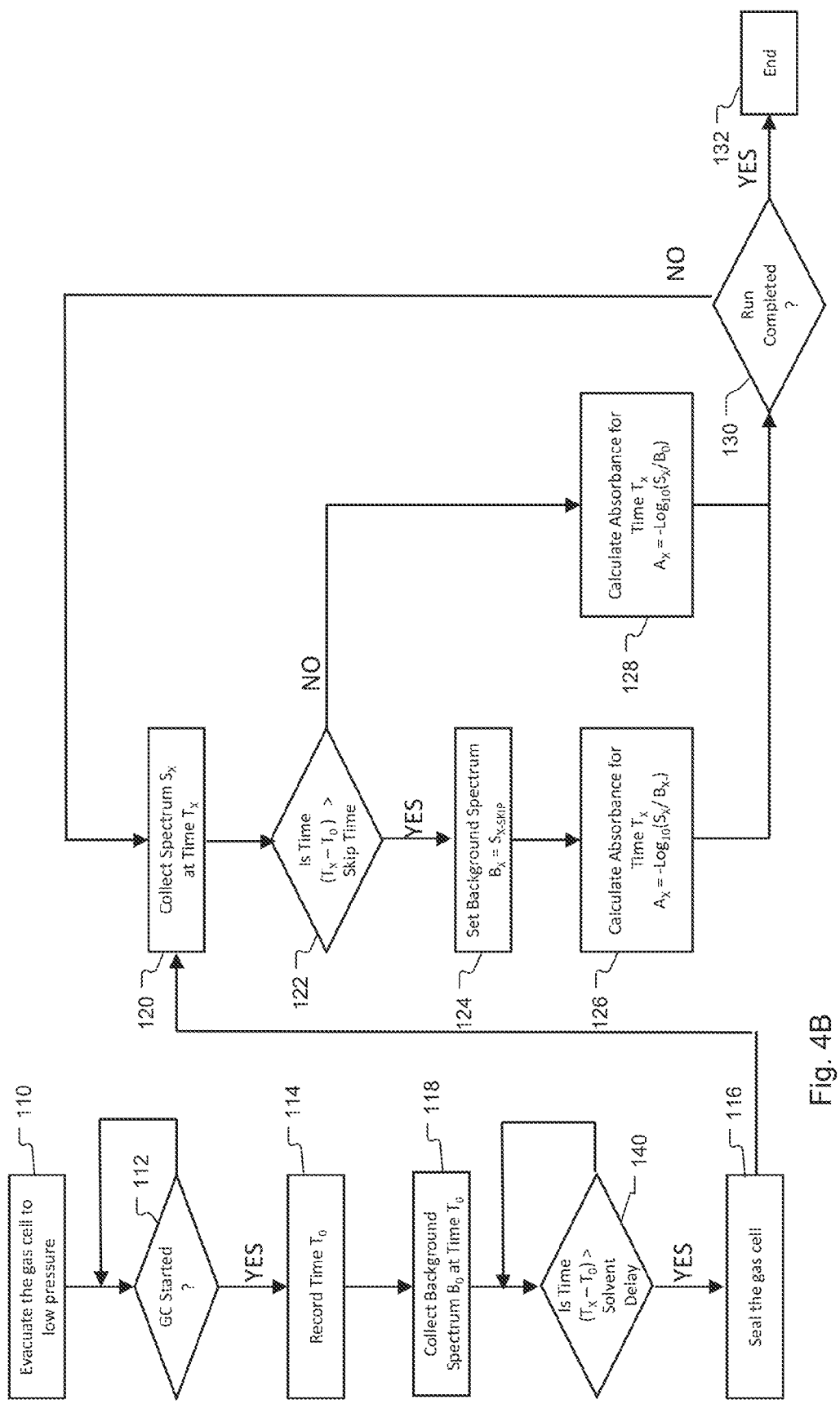
FIG. 4B is a flow diagram illustrating the control of the system 10 by the computer system 34 and determination of component absorbance spectra according to another embodiment.

FIG. 4B is a flow diagram illustrating the control of the system 10 by the computer system 34 according to another embodiment, which implements a solvent delay.

In general, many of the steps in this new flow diagram are similar to those in the previous diagram. Main difference is the implementation of the solvent delay in step 140. Specifically, the system runs with the valve 24 open and the vacuum pump 18 running for the "solvent peak delay" time period (Solvent Delay). This allows for the solvent (in the case of liquid injection) to flow from the column of the GC separator 12 to the gas cell 14, then out through the vacuum pump 18.

In some embodiments, during this "solvent delay" period, the system 10 continues acquiring and storing single beam spectra. The system 10 will also begin computing absorbance spectra=−Log (current single beam/background single beam). The computer system, by analyzing these spectra, can also determine when the solvent has been removed from the sample. It is also possible that the solvent could be diverted near or at the injection system depending on the sample and configuration, so that it never enters the GC column or enters a small length and then is split off.

Figure 4C:
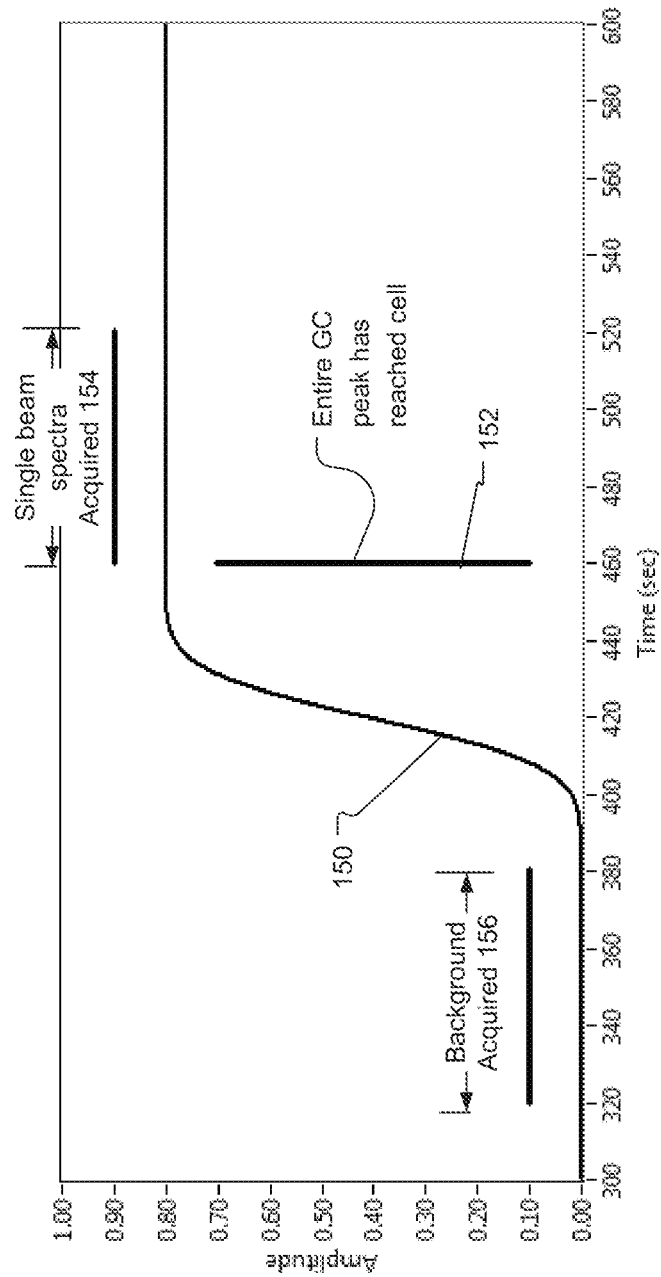
FIG. 4C is a schematic plot of concentration over time showing how background and current spectra are determined according to another implementation.

FIG. 4C illustrates the operation of some additional embodiments. In the previous discussed embodiments of FIGS. 4A and 4B, the absorbance at a given time is calculated based on the current detected spectra and a previously calculated background. In this current embodiment the absorbance calculations of step 126 are based on a current average of spectra and a background that is also typically calculated based on an average of spectra.

The plot represents the concentration profile in the cell 14 as a component comes out of the GC column or other separator and goes into the gas cell 14. Since the cell 14 integrates the components, i.e., is sealed, the concentration increases until the whole peak has reached the cell (see point 152). At that point in time, all of the component (e.g., compound) is in the cell 14. And, this event can be determined by having the computer system 34 monitoring how the spectra change over time and noting when successive spectra are undergoing little change with respect to each other. This can be performed in real-time or in a post experiment analysis.

Now the sample single beam spectra can be signal averaged for a period of time 154. Exemplary average times are generally between 10 seconds and 5 minutes, although they are more commonly between about 30 seconds and a few minutes. The start of this averaged spectrum is indicated by the elution time. Then the background is taken from a similar time-averaged signal 156 based on spectra that were taken before the elution of the peak into the cell 14.

The resulting absorption spectrum will contain only features due to the compounds that have been collected in the cell during this time.

Here, skip time would likely be chosen to be equal to or slightly larger than the time required for the chromatographic peak to elute completely. This would result in the background spectra being acquired before the peak begins to elute, and the sample spectra being acquired after the compound has completely eluted.

In general, the Skip Time can be fixed for the entire chromatography run, or it can be increased later in the run when chromatography peak are typical broader (the time required for the peak to completely elute from the column is longer due to diffusion during the residence time in the column). Normally, this results in reduced sensitivity since the broadened peaks have reduced peak intensity. With the present approach this is not the case since increasing the skip time still allows for the entire peak to be analyzed in a single measurement.

The sample averaging time 154 and background averaging time 156 need not be the same. If there are no other compounds eluting near the peak, then better sensitivity can be achieved by increasing either or both averaging time. Even if there are other peaks that elute nearby, spectral discrimination may still allow for increased averaging time.

In other embodiments, instead of calculating absorbance from two averaged single beams as described above, the method could use the stored initial background spectrum from the beginning of the chromatography run, or from any other suitable time for measuring a background when the cell is empty or purged. Then during the run, the conventional absorbance spectrum would be calculated from the averaged single beam sample spectrum and the stored initial background spectrum. This can be converted to the absorbance spectrum by subtracting the background absorbance spectrum using similar logic as described above for average and skip.

In practice, it is not known when the peaks will actually elute. Thus, in a one mode of operation, spectra will be acquired and stored during the run with a fairly short time interval, for example 1-2 seconds. Every 1-2 seconds a new absorbance spectrum can be calculated using the skip and average parameters, which can be fixed for the whole run, or varying with time as the run proceeds. Faster spectral data collection times in the range of 0.1 seconds are certainly possible for very fast GC experiments or when required due to the complexity of the sample.

In general, post analysis can also be performed, and this allows for optimization of skip and average parameters for specific chromatography peaks, or for specific eluting compounds. It may be advantageous to test results using longer or short skip time to be sure the whole peak has been capture by the current skip time. It may be useful to test longer averaging time in order to achieve more sensitive detection. It may be useful to test shorter averaging time in order to better reject interfering species that elute near the peak of interest. This logic allows the analysis to be optimized once an initial chromatogram is known.

Figure 4D:
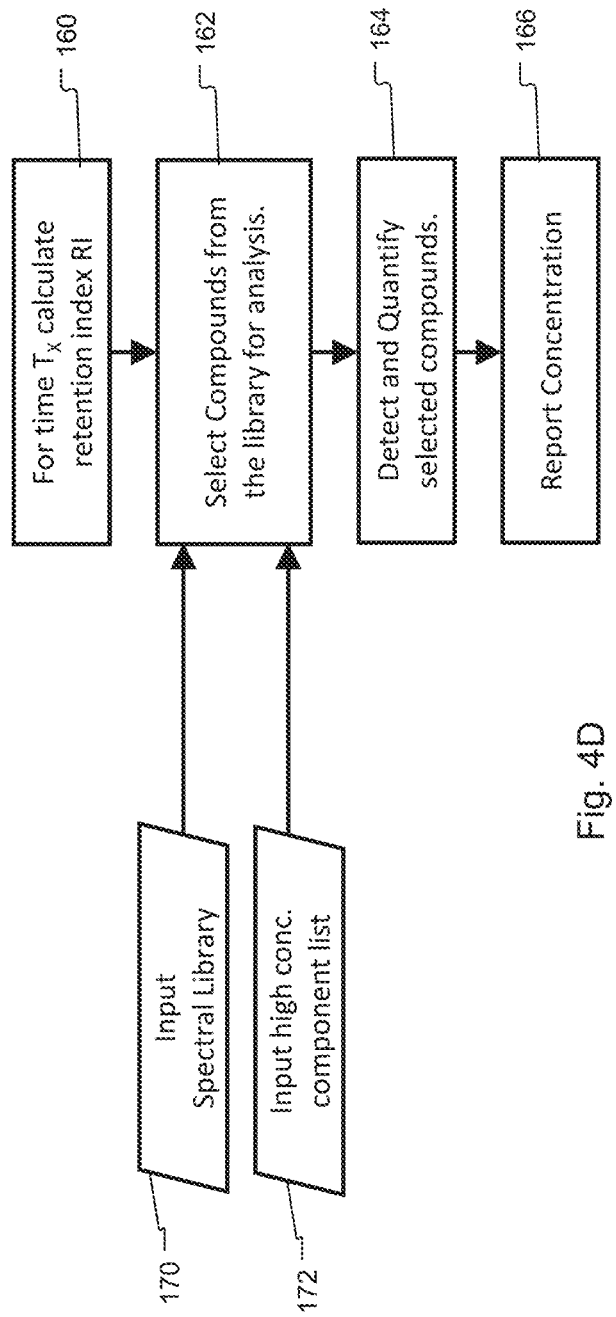
FIG. 4D is a flow diagram illustrating the analysis of the sample spectra to determine component concentrations.

FIG. 4D shows the analysis used to obtain the chromatographic results.

In more detail, in step 160, the retention index RI is calculated for sample times Tx. Then, in step 162, an input spectral library 170 and an input component list 172 are accessed. In general, the system will search for the components of interest by referencing the spectrum for those components.

Calibration spectra of the library 170 are stored for pure component compounds with the corresponding concentrations, desirable spectral regions for analysis, and spectral regions where there might be spectral interference with other compounds. Calibration spectra can also be stored with the retention index for the compound, which is an indicator of when the compound can be expected to elute from the column.

The computer system 34 usually selects a subset of the library calibration spectra and then performs quantitative analysis in step 164 to determine the concentration of these components. The quantitative analysis can be improved by excluding compounds from the library that are not present in the sample spectrum. The results are reported in step 166.

This can be done indiscriminately for each absorbance spectrum, thus producing results that look like a typical chromatogram. This can also be done by targeting specific compounds. In this case, it is desirable to choose the proper subset of the calibration library, and also to find the correct elution time, skip time, and average time for the analysis.

The first approach to choosing a subset of the library is based on elution time or retention index. Since the approximate time that a given compound in the library will elute from the column is known, the computer system 34 starts by only considering compounds that are likely to elute for the elution time of the sample spectrum being analyzed.

There will also be compounds that should be included over a larger range of time than the expected elution time. For example, water and carbon dioxide may always be present, and the solvent used for liquid injections and high concentration components may be present in the spectrum for several minutes after the solvent peak starts eluting. Further components are also monitored for decreases due to condensation so that they do not interfere with analysis. They would show up as a negative concentration.

After reducing the list of possible compounds, quantitative analysis on the sample spectrum is performed by the computer system to determine concentrations of these compounds in the sample spectrum. If any of the compounds are determined to not be present, then they are removed from the list and the analysis can be repeated with the further reduced list of compounds. Alternatively, the list can be tested one-by-one before analysis to determine if the compounds are present. The analysis can then be performed using the only those library component detected to be present in the sample spectrum.

The presentation of results by the computer system 34 is often in a compound specific chromatogram format, concentration or mass versus time for each compound. This could also be converted to a combined chromatogram format, concentration or mass versus time for all compounds. In general, the peak height of each peak corresponds to the total concentration or mass of the corresponding compound. The peak area is only indicative of the time period during which the compound elutes from the column.

The results could also be presented in a "stick" plot format, where the mass or concentration of each compound detected is plotted as a single point versus time or retention index.

Some of the embodiments disclosed herein utilize separation techniques that do not rely on gas chromatography. In many cases, such techniques can be used since procedures related to data collection, data handling and data analysis described herein do not require fully resolved chromatographic peaks. Particular applications that can benefit from eliminating the use of the GC include but are not limited to analyses of semi-volatile and non-volatile species; analyses of some inorganics that do not chromatograph well; analyses of mixed samples (organic, inorganic, VOC, SVOC, non-volatile) that typically require column choices and/or changes; and others. Considering that GCs can be viewed as a very controlled distillation (with 10,000-100,000's of theoretical plates), and taking into account that full resolution of peaks is not required in practicing aspects of the invention, a GC separator such as described above can be replaced by a distillation-based or "pseudo distillation" separator, as further described below. During operation, a pseudo distillation separator can first remove the highest component, e.g., the solvent. Once this is accomplished, the quantitative levels of chemicals that can be measured decreases linearly with the increase in the sample size.

Figure 5:
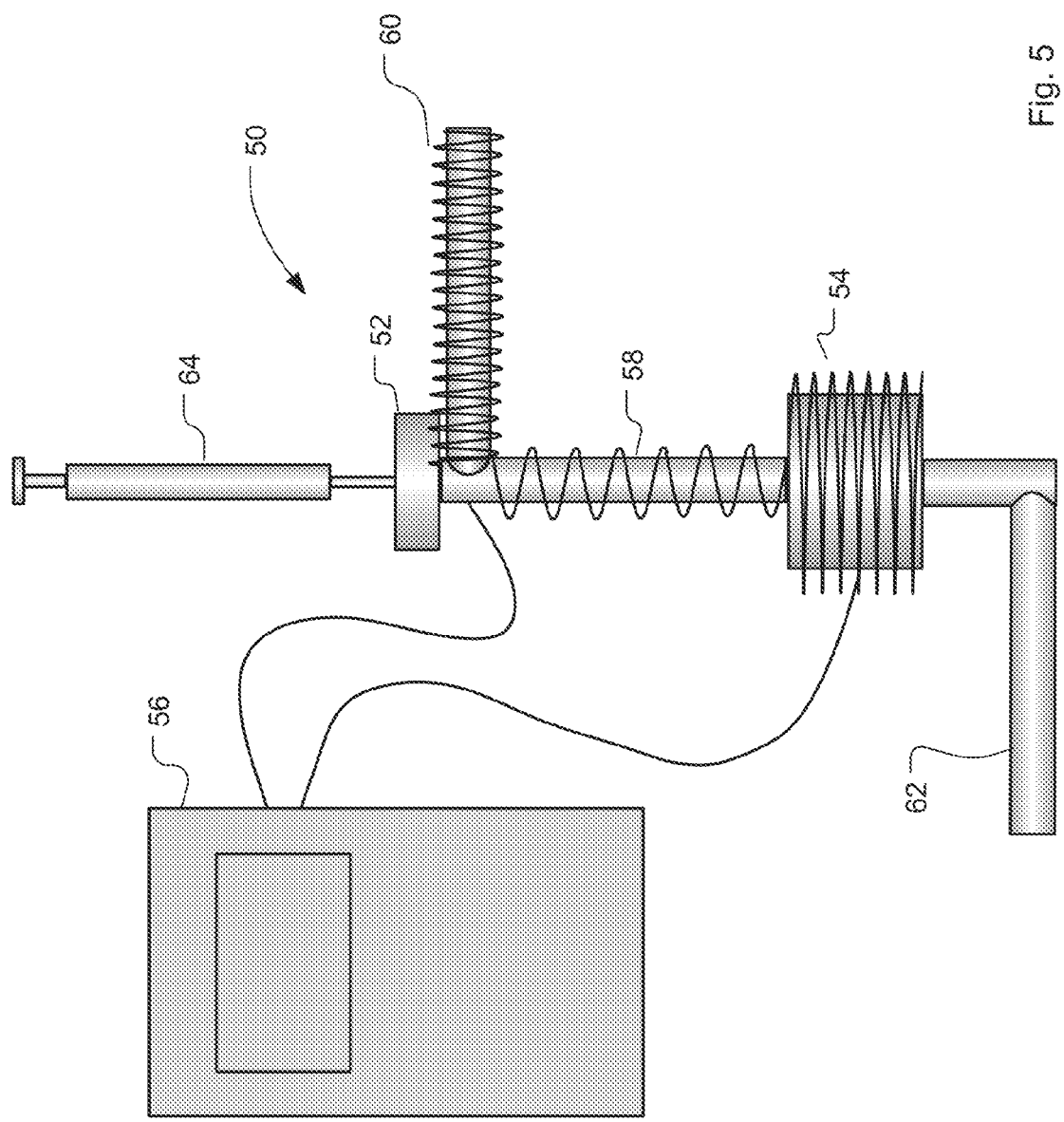
FIG. 5 is a schematic diagram of a distillation-based separator.

Shown in FIG. 5, for example, is distillation-based separator 50 that is used in place of the gas chromatograph (GC) separator 12 shown in FIGS. 2A and 2B.

The separator 50 includes injection port 52, for receiving a sample that typically includes a solvent, sample vaporization chamber 54 and computer system 56 monitoring and/or controlling the temperature.

In many implementations, sample port 52 is configured to accommodate relatively large injection volumes, e.g., of the order of milliliters (mL), such as 1 mL, rather than the typical 1 µL sample common with GC-MS injection volumes. The port can be maintained at a temperature suitable for removing the solvent and retaining the compounds of interest.

A relatively small tube, e.g., ⅛ inch, 1/16 inch OD, that is a few inches long, preferably fabricated from stainless steel or another material (metal, alloy and so forth) with the potential of an inert coating, having low heat transmission properties, can serve as distillation column 58. Typically, such an arrangement is capable of separating components without problems stemming from chemical interaction with the mobile or stationary phases typical of chromatographic separations. The tube can be hollow or can contain a packing material, e.g., glass beads. Interior surfaces of the tube can be smooth or roughened to increase the number of theoretical plates. PVT or PTV can be used to perform a similar function.

Taking advantage of the poor heat propagation through the tube material (stainless steel for instance), heating the vaporization chamber 54 to higher temperatures than tube 58, e.g., 300° C., generates a gradient temperature that extends along the tube, to the sample port 52. This change in temperature along the length of the tube is expected to generate a large number of potential "theoretical plates" inside the tube 58. Raising or lowering the temperature applied to 54 and 58 determines which materials come off the column. The number of "theoretical plates" could be determined by separating a number of VOC and SVOC mixtures. The information can then be used to optimize the heating configuration.

Heating and cooling can be conducted using a thermoelectric (also known as a Peltier) device (the principle of which relies on heat transfer from one side of a solid state device to the other, with consumption of electrical energy). By changing the DC voltage the device can be switched from cooling to heating to remove the solvent and eventually the compounds initially present in the solvent.

The temperature of the heated transfer line 60 also can be raised so that heating is on both sides of the column 58 which would change the dynamic of the temperature profile across the column 58. The column may be provided with a jacket not shown in FIG. 5 that can be pulled over the column 58 from the hot vaporization chamber end 54 to heat the whole tube to a certain temperature in order to remove compounds with the highest boiling points.

Heated transfer line 60 connects distillation separator 50 to the sample cell 14 described previously with a suitable detection and/or analysis device, while conduit 62 provides optional carrier gas flow. The sample typically including a solvent can be introduced via syringe 64.

A distillation-based (or pseudo-distillation) separator such as described above is connected to the sample cell 14. The spectral detection/analysis device such as an FTIR, another optical spectrometer or detection means is then used to analyze the components in the cell 14 as describe above. In some cases, it can even be coupled to a MS device (particularly if sufficient theoretical plates can be generated to produce adequate peak separations).

In other implementations, the exhaust of the pseudo distillation separator is connected to a GC, for instance GC 12 in FIG. 2. In the latter case, the pseudo distillation separator can be used, for instance, to vaporize solvent while capturing volatiles and semi volatiles in the tube. The retained compounds can be then separated by the GC.

Figure 6:
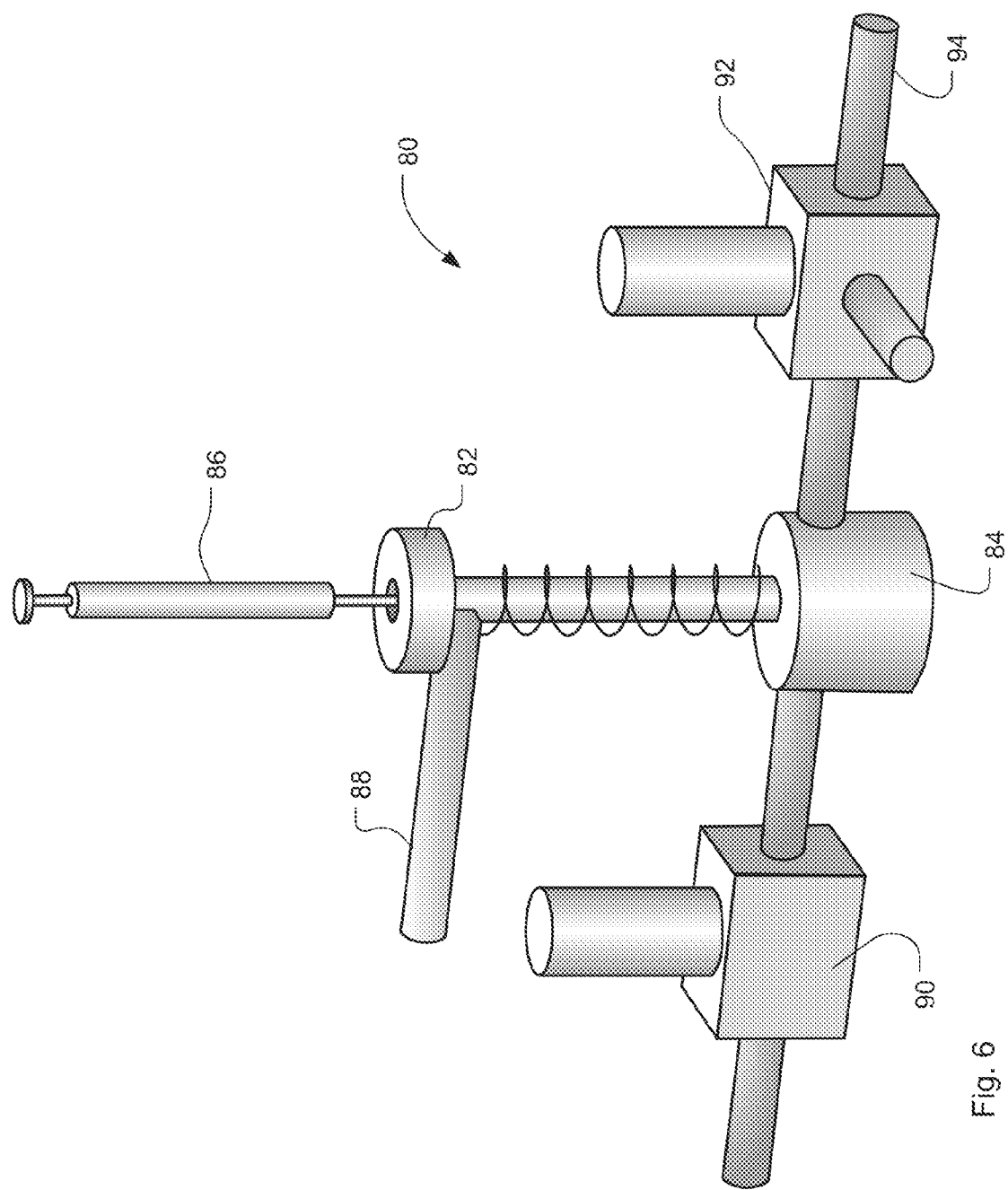
FIG. 6 is a schematic diagram of a high volume injection assembly.

Shown in FIG. 6 is high volume injection assembly 80 including septa-containing injection port 82, typically held at low heat conditions, and stepped vaporization chamber 84, first eluting the solvent and then quickly vaporizing all the analytes. The sample can be introduced via syringe 86. Again, this can be similar to PVT or PTV.

Conduit 88 provides septum purge and column flow gas. Valve 90 can be used to vent vaporized solvent or direct the vaporized solvent to a solvent capture system. The sample is then directed to sample transport valve 92 from which it can pass, via conduit 94, to a separation device like a GC with a detection and/or analysis device described herein. Conduit 94 can be provided for secondary column flow for the GC or other separation device during the sample preparation process.

In another possible arrangement, solvent vapor is analyzed for solvent and solute content. In this implementation, the exhaust of valve 90 is directed to the FTIR to determine what is coming off with the solvent. A valve or another suitable device can be used to divert gas from going to the sample cell, thus preventing solvent from going backwards through the GC. Since generally there are not that many compounds that co-elute or in this case vaporize with the solvent at low vaporization temperatures, the lack of separation is not thought to present problems. This same form of solvent diversion to the gas cell could be achieved with a properly configured PVT or PTV.

Embodiments disclosed herein can have many applications and could be used or adapted for ambient air collection for VOCs or other chemicals, home air collection, in particular in cases in which cost is an issue, potentially for obtaining multiple samples simultaneously, personal exposure monitor in the work place or other indoors environments, for semi-volatile analysis (pesticides, herbicides, drugs in urine, nicotine, etc.), medical tests, for drug purity testing, e.g., in the pharmaceutical industry, and others. In specific applications, the system described herein is connected to sample collection devices such as TDT, liquid, solid, purge and trap or other devices, and so forth.

The following non-limiting examples are provided to illustrate principles of the invention.

Example 1

In a conventional GC-FTIR configuration, the gas leaves the GC and passes through the FTIR gas cell (usually a light pipe that is generally around 10 to 20 cm long) in a few seconds. If the concentration of a chemical compound is high enough, what is observed is a peak that rises and then falls, a behavior typical of any other detector. In contrast, using a system such as the system of FIGS. 2A and 2B, the gas can be collected in the gas cell for integration of each peak eluted from the GC.

A multiple path length gas cell can be utilized to generate a much higher absorbance since in the configuration described herein response time of the gas through the cell is not a concern. The absorbance increases linearly with the increased path length. Thus increasing the path length from a length of 10 cm (the actual length of the cell) to a multiple path of 5 m will produce a 50 times greater absorbance, assuming the same concentration in the in the sample cell described herein and a conventional lightpipe. (Typically, a light pipe will have a higher concentration since the gas emerging from the GC is not diluted due to expansion in the sample cell.) A particular implementation that could result in a significant improvement (e.g., 50 times greater absorbance) relates to embodiments deployed for source testing, where the gas just flows through the multiple pass gas cell normally and gases are measured (ppm to ppb). In comparison, a light pipe would not give a low enough measurement (high ppm at best).

While the gas is being monitored, a portion from the incoming flow or outgoing flow can be collected and concentrated on a TDT. The TDT then can be desorbed through the GC to get lower detection limits. The improved detection limit will be based on the number of cell volumes. So for a collection of 60 min at 200 mL/min being trapped there will be a 60 fold enhancement in the absorbance if all the gases are trapped since the gas cell is 200 mL. A further improvement can be obtained by running at lower resolution since the GC carries out the separation. The results may be similar to those obtained with a lightpipe due to the same lower resolution.

The more significant advantage, however, resides in the flexibility of running in the direct gas analyzer mode or as a TDT/GC/FTIR. Since both modes are available, each can be used as needed by source testers. This is not possible with a conventional lightpipe.

Once the spectra are collected or even during data collection, raw single-beam spectra can be obtained and averaged over 1 to 2 minutes by the computer system. (The experiment also could be conducted by using calculated absorbance spectra but a higher noise level might be encountered.) Increasing the time from a typical 1 sec to 1 minute can result in about 8 times better MDL. Combining a multiple pass arrangement with the integration-averaging approach described herein can more than make up for any losses due to the increase in sample cell volume (compared to a traditional lightpipe approach). Improved mirror coatings, resulting in further increases in pathlength, can provide additional enhancements in detection limits. For example, a highly reflective coating could allow for 40 to 80 m in the same volume. Such coatings are entirely feasible with a sample (gas) cell that is only connected to a GC, where problems related to the deposition of dust or compounds on the mirror are reduced or minimized.

Since the spectra for each compound are collected after the entire analyte is in the sample cell a further sensitivity enhancement is gained from maybe 2 or 3 times for an early eluting peak to one that could be an order of magnitude more sensitive for a late eluting peak that is spread over several minutes.

Based on experience with the apparatus and techniques described herein, integrating can provide an improvement in sensitivity by a factor of 3 and integrating by a factor of 8, with additional benefits due to path length increases, to an overall demonstrated improvement of 24×.

Figure 8:
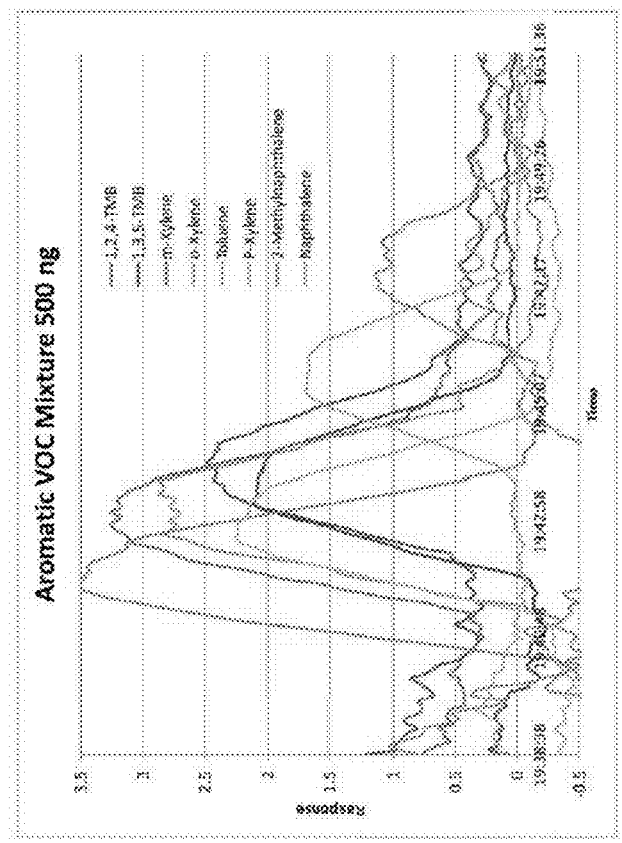
FIGS. 7-11 are plots obtained by practicing aspects of the invention.
Figure 7:
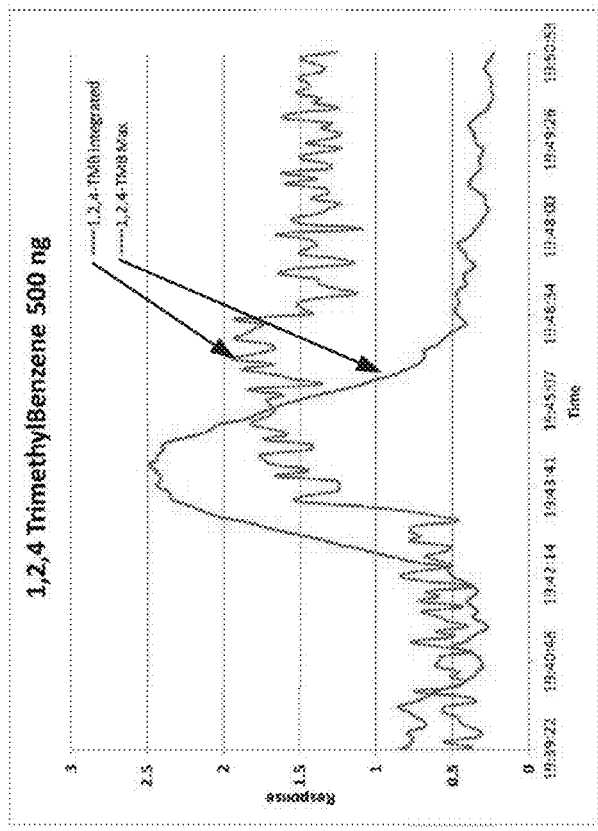

Starting with the original background spectrum to calculate the absorbance spectrum, the background can be changed as more and more data were collected. So, the background data starts to move a minute or two behind the data collection. Expressed in a different way, the background spectrum occurs a minute or two before each peak. If the background is far enough ahead of each peak, the signal should go up, level off and then start to decrease. Eventually the background moves through each peak and each peak disappears into the background. Thus the gases in the background only need to be stable in concentration over the time used as a background (1 or 2 minutes) and not the entire experiment. While the moving background may not per se provide significant SNR advantages, it removes the earlier compounds by folding them into the background spectrum over time. This is shown in FIGS. 7 and 8 where the analyte peaks goes up, flatten out and then decrease. The flattened region may be increased by widening the separation time between the background and sample.

As seen in FIG. 7, one compound, 1,2,4-trimethylbenzene (1,2,4-TMB) was selected from a mixture of aromatic VOCs. When the mixture is run through a sample cell (not contained or integrated) having a multiple path of 5.11 m for a few seconds, this particular compound was not detected and all that was observed was noise. The noisy plot shown here is an integration of the 1,2,4-TMB signal, where the compound was contained in the gas cell for the duration of the measurement, just above the noise level.

In the other curve of FIG. 7, the spectral data were averaged for approximately 1 minute. In addition, a moving spectral background was used that was approximately 1 min in length. This could be thought of as taking a derivative of the integrated signal. The results in FIG. 7 demonstrate that the processed signal was 20+ times the noise level now, from data that was initially only barely above its detection or not detected when performed in a traditional transient detection methodology. The results illustrate the power of the basic technique. Further improvements in MDL can be obtained by optimizations such as discussed above.

With detector optimization for the resolution and spectral range used for collecting the spectral data, the signal to noise or MDL can be improved by a factor of 10 to 12. Practicing aspects of the invention allows detection of 1,2,4-TMB at the 2.5 ng level.

Moreover, since the size of the sample no longer matters because the solvent can be boiled off without affecting e.g., MS detection, much larger samples can be run so that even smaller absolute concentration of the sample can be measured. Detection of the order of 1 ppt levels or lower could be expected, depending on the compound. Thus in contrast to a conventional light pipe, which watches a peak come and go and would draw out the peak, the techniques described herein rely on peak integration.

In contrast to MS, the spectroscopic technique described herein can also measure different isomers of xylenes and trimethylbenzenes (as shown in FIG. 8); can measure compounds as they co-elute (MS can only handle a couple simultaneously, if these compounds have different spectra); and can measure as many as 10 to 20 compounds simultaneously even if they are similar.

The SNR or MDL could be optimized to detect 10's pg of elutant, with further possible improvements provided by appropriate mirror coatings and gas cell configurations. Further benefits are expected with software configured so that the algorithm or protocol is constantly changing the compounds to be detected. Since the compounds will be coming off at a specific index or retention time, the software will know which compounds to analyze for and when.

Also, using FTIR (rather than MS) has the advantage that all library data will be both qualitative and quantitatively correct. So the library can be used not only to identify but also to quantify. Moreover, any calibration generated will be fixed for every system. In contrast, since a MS library can only qualify, calibrations must be run to quantify. Typically, MS calibrations need to be re-checked frequently.

Example 2

These experiments were undertaken to demonstrate spectral aspects of the techniques described herein. A couple of screenshots of the fingerprint region of the IR spectrum from 550-1250 $cm^{-1}$ were taken to demonstrate how the spectra change after post processing as described herein.

Figure 9:
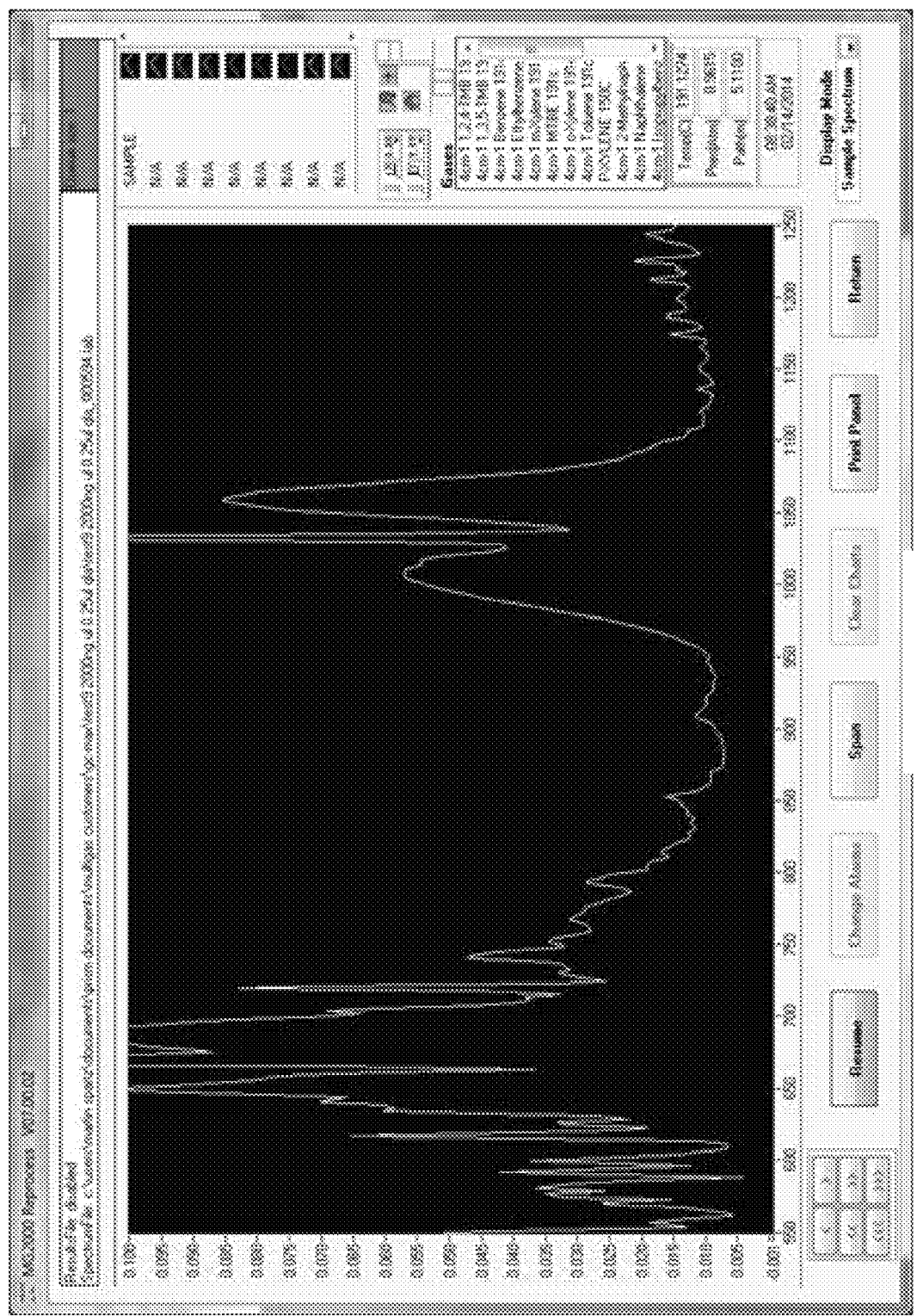

The graph in FIG. 9 is a final raw spectrum after a mixture of 60+ gases (compounds) is collected in the gas cell. Many of the gases were chlorinated and have strong absorption peaks at the low frequency end of the spectrum. All the features observed below 850 $cm^{-1}$ are absorption peaks by some of the 60+ compounds. The peak PQR structure at 950-1150 $cm^{-1}$ is indicative of the methanol which was the solvent.

Trying to analyze a spectrum for 60+ compounds with existing techniques, even when possible, proves to be exceedingly difficult, especially if identifying other unknowns is also desired.

Figure 10:
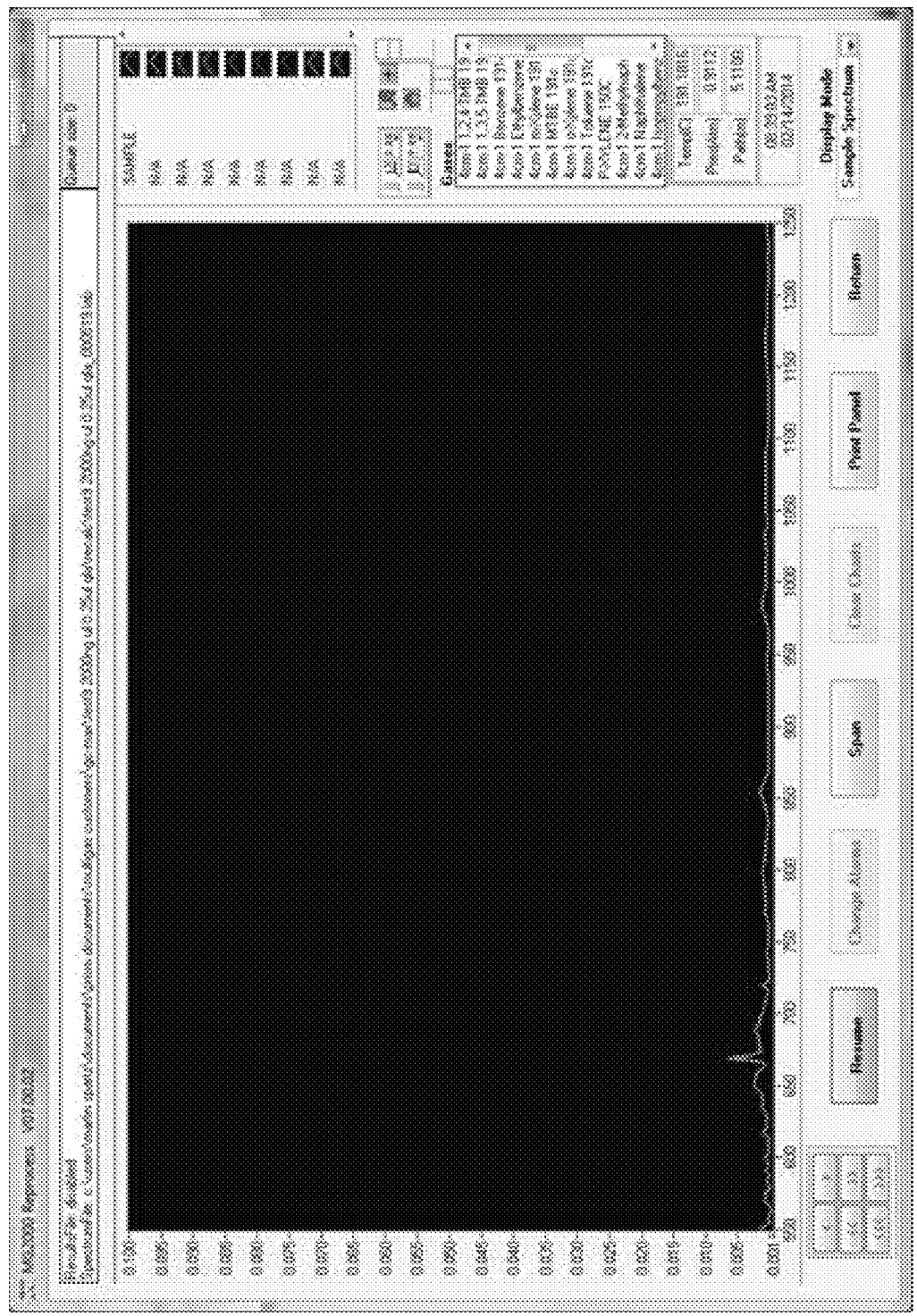

If, however, protocols or algorithms described herein are applied across the data and inspecting one of the later spectra shows that most of the chlorinated compounds and the solvent methanol are no longer present even though they are still present in the gas cell. FIG. 10 is on exactly the same x and y scale as FIG. 9, and shows how well the background interfering compounds and solvent can be removed by the computer system. Only a few small features are observed.

At this point, the FTIR multivariate analysis software and library database can be used by the computer system to identify the remaining major and smaller minor peaks.

Figure 11:
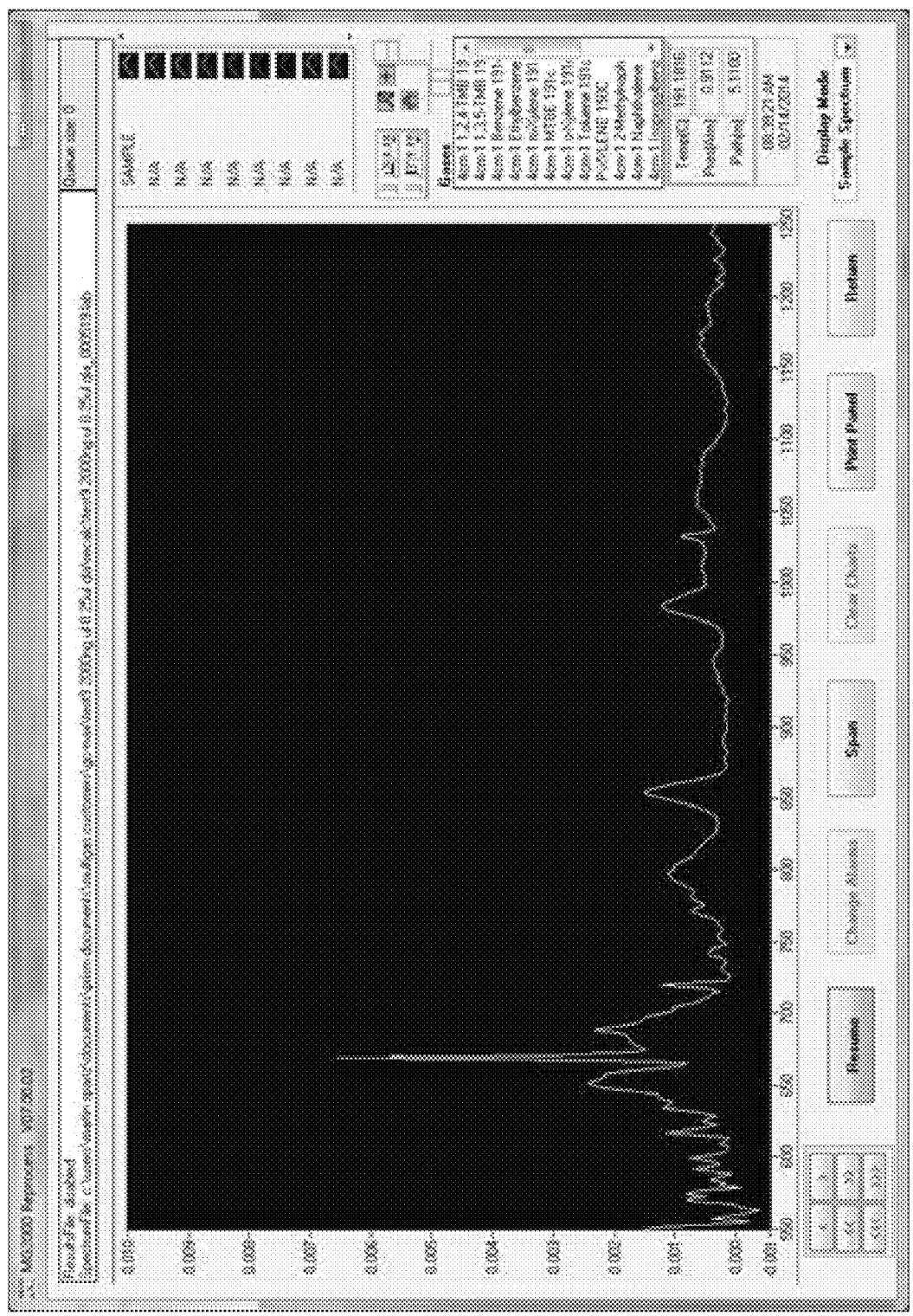

If this spectrum is expanded by a factor of 10 (FIG. 11), one can observe the infrared absorption features and these can be easily analyzed, especially when using a FTIR library (e.g., of 1000s of compounds) in conjunction with calling compounds at the appropriate time in the GC elution. Spectral searching can also be done to call spectra if needed.

Importantly, with techniques such as those described herein, it is possible to look at high concentration as well as low concentration compounds that co-elute as long as the two have some difference in spectral features. Advantageously, almost all compounds, even cis and trans isomers have unique infrared spectra.

While this invention has been particularly shown and described with references to preferred embodiments thereof, it will be understood by those skilled in the art that various changes in form and details may be made therein without departing from the scope of the invention encompassed by the appended claims.

What is claimed is:

1. A sample analysis system, comprising:
    a gas chromatography system from which components of a sample elute over time;
    a sample cell, which has been partially or fully evacuated, in which the components are collected;
    a Fourier transform infrared spectrometry system for obtaining current infrared spectra of the components in the sample cell; and
    a computer system that receives the current infrared spectra detected by the Fourier transform infrared spectrometry system and maintains background infrared spectra that include infrared spectra from previously eluted components and analyzes currently eluting components with reference to the background infrared spectra.

2. A system as claimed in claim 1, wherein the Fourier transform infrared spectrometry system measures absorption spectra.

3. A system as claimed in claim 1, wherein a path length in the sample cell is increased by a multiple path optical arrangement.

4. A system as claimed in claim 1, wherein the sample cell includes a White cell or modified White cell type optical arrangement.

5. A system as claimed in claim 1, further comprising a vacuum device for fully evacuating or partially evacuating the sample cell.

6. A system as claimed in claim 1, further comprising a valve for isolating the sample cell from a pumping device, a valve for diverting output from the separator away from the sample cell, a sample cell pressure control, or any combination thereof.

7. A system as claimed in claim 1, further comprising a sample concentrating device for collecting the sample before the gas chromatography system.

8. A system as claimed in claim 7, wherein the sample concentrating device is a TDT, purge and trap or a solvent concentrating device.

9. A system as claimed in claim 1, further comprising automated instrument controls.

10. A system as claimed in claim 9, wherein the instrument controls execute procedures for accessing information on known compounds, integration procedures, correction procedures, compound information libraries, calibrations, internal standards, or any combinations thereof.

11. A sample analysis method, comprising:
  providing components of a sample over time with a gas chromatography system;
  partially or fully evacuating a sample cell;
  collecting the components in the sample cell; and
  obtaining current infrared spectra of the components in the sample cell with a Fourier transform infrared spectrometry system; and
  maintaining background infrared spectra that include infrared spectra from previously eluted components and analyzing currently eluting components with reference to the background infrared spectra.

12. A method as claimed in claim 11, wherein obtaining the current infrared spectra comprises obtaining absorption spectra.

13. A method as claimed in claim 11, further comprising directing electromagnetic radiation in the sample cell along multiple paths.

14. A method as claimed in claim 11, further comprising drawing at least a partial vacuum on the sample cell and sealing the sample cell to accumulate the components.

* * * * *